(12) United States Patent
Weaver et al.

(10) Patent No.: US 11,519,859 B2
(45) Date of Patent: Dec. 6, 2022

(54) RHODOL-BASED THALLIUM SENSORS FOR HIGH-THROUGHPUT SCREENING OF POTASSIUM CHANNELS

(71) Applicant: Vanderbilt University, Nashville, TN (US)

(72) Inventors: Charles David Weaver, Nashville, TN (US); Brendan F. Dutter, Nashville, TN (US); Gary A. Sulikowski, Nashville, TN (US)

(73) Assignee: Vanderbilt University, Nashville, TN (US)

(*) Notice: Subject to any disclaimer, the term of this patent is extended or adjusted under 35 U.S.C. 154(b) by 519 days.

(21) Appl. No.: 16/379,100

(22) Filed: Apr. 9, 2019

(65) Prior Publication Data
US 2019/0308991 A1 Oct. 10, 2019

Related U.S. Application Data

(60) Provisional application No. 62/655,184, filed on Apr. 9, 2018.

(51) Int. Cl.
*G01N 21/64* (2006.01)
*G01N 33/68* (2006.01)
(Continued)

(52) U.S. Cl.
CPC ....... *G01N 21/6428* (2013.01); *C07D 493/10* (2013.01); *C09B 11/245* (2013.01);
(Continued)

(58) Field of Classification Search
CPC .............. C09B 11/245; C07D 493/10; G01N 21/6428; G01N 2021/6439; G01N 33/6872; G01N 33/84
See application file for complete search history.

(56) References Cited

U.S. PATENT DOCUMENTS 6,162,931 A * 12/2000 Gee ..................... C07C 37/055
430/345
9,103,791 B1  8/2015 Weaver
(Continued)

FOREIGN PATENT DOCUMENTS

WO   WO-2017122799 A1 * 7/2017 ............. C09K 11/06

OTHER PUBLICATIONS

Ramos-Hunter, Susan Joanne "Development of Molecular Tools for the Investigation of G protein-gated Inwardly Rectifying Potassium (GIRK) Channels," Vanderbilt University. ProQuest Dissertations Publishing, 2017. 10753408. (Year: 2017).*
(Continued)

*Primary Examiner* — Jennifer Wecker
*Assistant Examiner* — Michelle Adams
(74) *Attorney, Agent, or Firm* — Michael Best & Friedrich LLP

(57) ABSTRACT

Provided are novel rhodol-based compounds, the preparation method thereof, and use thereof in $Tl^+$ flux assays. The fluorescent thallium ion sensor compounds have a rhodol fluorophore attached to an amino dicarboxylic acid metal binding moiety. The compounds are prepared in the "pro-dye" form, with the rhodol oxygen and the carboxylic acids of the metal binding unit masked by protecting groups. The disclosed compounds may be used as more red-shifted and less pH-sensitive variants of Thallos.

18 Claims, 7 Drawing Sheets

(51) Int. Cl.
C07D 493/10 (2006.01)
C09B 11/24 (2006.01)
G01N 33/84 (2006.01)

(52) U.S. Cl.
CPC ......... *G01N 33/6872* (2013.01); *G01N 33/84* (2013.01); *G01N 2021/6439* (2013.01)

(56) References Cited

U.S. PATENT DOCUMENTS

| | | | |
|---|---|---|---|
| 2010/0279314 A1* | 11/2010 | Beacham | G01N 33/84 435/7.8 |
| 2019/0094248 A1* | 3/2019 | Hirose | G01N 33/84 |
| 2019/0187155 A1* | 6/2019 | Beacham | C07D 493/10 |

OTHER PUBLICATIONS

Hammershøj et al., "Facile Large Scale Synthesis of 5- and 6-Carboxyfluoresceins: Application for the Preparation of New Fluorescent Dyes", European Journal of Organic Chemistry, 2015, pp. 7301-7309.
West et al., "Dynamic Combinatorial Libraries of Disulfide Cages in Water", Organic Letters, vol. 7, No. 13, 2005, pp. 2615-2618.
Ackerman et al., "Mechanisms of Disease" The New England Journal of Medicine, vol. 336, No. 22, 1997, pp. 1575-1586.
Lüscher et al., "Emergine roles for G protein-gated inwardly rectifying potassium (GIRK) channels in health and disease", Nature Reviews Neuroscience, vol. 11, May 2010, pp. 301-315.
Quayle et al., "ATP-Sensitive and Inwardly Rectifying Potassium Channels in Smooth Muscle", Physiological Reviews, vol. 77, No. 4, 1997, pp. 1165-1232.
De Leon et al., "Mechanisms of Disease: advances in diagnosis and treatment of hyperinsulinism in neonates", Nature Clinical Practice Endocrinology & Metabolism, vol. 3., No. 1, 2007, pp. 57-68.
Welling et al., "A comprehensive guide to the ROMK potassium channel: form and function in health and disease", Am. J. Physiol Renal Physiol., 2009, 297, F849-F863.
Choe, "Potassium Channel Structures", Nature Reviews Neuroscience, vol. 3, Feb. 2002, pp. 115-121.
Schmitt et al., "Cardiac Potassium Channel Subtypes: New Roles in Repolarization and Arrhythmia" Physiol. Rev., 2014, 94, pp. 609-653.
Maljevic et al., "Potassium channels: a review of broadening therapeutic possibilities for neurological disease", Journal Neurolology, 2013, 260, pp. 2201-2211.
Ashcroft, "ATP-sensitive K+ channels and disease: from molecule to malady", American Journal of Endocrinology, 2007, pp. E880-E889.
Weaver et al., "A Thallium-Sensitive Fluorescence-Based Assay for Detecting and Characterizing Potassium Channel Modulators in Mammalian Cells", Journal Biomolecular Screening, 2004, 9, pp. 671-677.
Li et al., "Identification of novel KCNQ4 openers by a high-throughput fluorescence-based thallium flux assay", Analytical Biochemistry, 2011, 418, pp. 66-72.
Yue et al., "Novel KCNQ2 channel activators discovered using fluorescence-based and automated patch-clamp-based high-throughput screening technniques", Acta Pharmacologica Sinica, 2016, 37, pp. 105-110.
Raphemot et al., "Development and Validation of Fluorescence-Based and Automated Patch Clamp-Based Functional Assays for the Inward Rectifier Potassium Channel Kir4.1", Assay and Drug Development Technologies, vol. 11, No. 9/10, 2013, pp. 532-543.
Gill et al., "A High-Throughput Screening Assay for NKCC1 Cotransporter Using Nonradioactive Rubidium Flux Technology", Assay and Drug Development Technologies, vol. 15, No. 4, 2017, pp. 167-177.

Weaver et al., "Thallium Flux Assay for Measuring the Activity of Monovalent Cation Channels and Transporters", Methods in Molecular Biology, 2018, vol. 1684, pp. 105-114.
Carter et al., "Fluorescent Sensors for Measuring Metal Ions in Living Systems", Chemical Reviews, 2014, 114, pp. 4564-4601.
Chang et al., "Bright Fluorescent Chemosensor Platforms for Imaging Endogenous Pools of Neuronal Zinc", Chemistry & Biology, vol. 11., Feb. 2004, pp. 203-210.
Simeonov et al., "Flourescence Spectroscopic Profiling of Compound Libraries", J. Med. Chem., 2008, 51, pp. 2363-2371.
Minta et al., "Flourescent Indicators for Cytosolic Calcium Based on Rhodamine and Flourescein Chromophores", The Journal of Biological Chemistry, vol. 264, No. 14, May 1989, pp. 8171-8178.
Sensi et al., "A new mitochondrial fluorescent zinc sensor", Cell Calcium, 2003, 34, 281-284.
Whitaker et al., "Flourescent Rhodol Derivatives: Versatile, Photostable Labels and Tracers", Analytical Biochemistry, 1992, 207, pp. 267-279.
Kamino et al., "Design and synthesis of regioisomerically pure unsymmetrical xanthene derivatives for staining live cells and their photochemical properties", Bioorganic Medicinal Chemistry Letters, 2008, 18, pp. 4380-4384.
Dodani et al., "Copper is an endogenous modulator of neural circuit spontaneous activity", Proc. Natl. Acad. Sci. U. S. A., vol. 111, No. 46, Nov. 2014, pp. 16280-16285.
Poronik et al., "Nonlinear Optical Chemosensor for Sodium Ion Based on Rhodol Chromophore" Journal of Organic Chemistry, 2013, 78, pp. 11721-11732.
Contractor et al., "Imaging Ca(2+) with a Flourescent Rhodol" Biochemistry, 2017, 57, pp. 237-240.
Peng et al., "Construction of a Library of Rhodol Fluorophores for Developing New Flourescent Probes", Organic Letters, vol. 12, No. 3, 2010, pp. 496-499.
Grimm et al., "A general method to fine-tune fluorophores for live-cell and in vivo imaging", Nature Methods, vol. 14, No. 10, 2017, pp. 987-994.
Kaufmann et al., "ML297 (VU0456810) the First Potent and Selective Activator of the GIRK Potassium Channel, Displays Antiepileptic Properties in Mice", ACS Chemical Neuroscience, 2013, 4, pp. 1278-1286.
Niswender et al., "A Novel Assay of G(i/o)-Linked G Protein-Coupled Receptor Coupling to Potassium Channels Provides New Insights into the Pharmacology of the Group III Metabotropic Glutamate Receptors", Molecular Pharmacology, 2008, 73, pp. 1213-1224.
Schroeder et al., "IonWorks™ HT: A New High-Throughput Electrophysiology Measurement Platform", Journal of Biomolecular Screening, 2003.,8, pp. 50-64.
Du et al., "Development and Validation of a Thallium Flux-Based Functional Assay for the Sodium Channel NaV1.7 and Its Utility for Lead Discovery and Compound Profiling", ACS Chemical Neuroscience 2015, 6, pp. 871-878.
Chen et al., "2-Hydroxy benzothiazole modified rhodol: aggregation-induced emission and dual-channel fluorescence sensing of Hg(2+) and Ag(+) ions", Sensors Actuators B Chem. 2018, 255, pp. 2086-2094.
Zhang et al., "A simple yet effective fluorescent probe for detecting and imagine mercury ions in cells", RSC Advances, 2015, 5, pp. 20634-20638.
Wechakorn et al., "Rhodol-based fluorescent probe for Au(3+) detection and its application in bioimaging", RSC Advances 2016, 6, pp. 24752-24755.
Taki et al., "A mitochondria-targeted turn-on flourescent probe based on a rhodol platform for the detection of copper", Organic and Biomolecular Chemistry, 2014, 12, pp. 4999-5005.

* cited by examiner

-- PRIOR ART --

RHODOL-BASED THALLIUM SENSORS FOR HIGH-THROUGHPUT SCREENING OF POTASSIUM CHANNELS

CROSS-REFERENCE TO RELATED APPLICATIONS

This application claims the benefit of U.S. Provisional Patent Application No. 62/655,184, filed Apr. 9, 2018, which is incorporated herein by reference in its entirety.

TECHNICAL FIELD

The present invention relates to novel rhodol-based compounds and their use in measuring the activities of ion channels in a cell.

BACKGROUND

Ion channels are pore-forming membrane proteins which promote the passage of ions across cellular membranes. Within the superfamily of ion channels are subfamilies with different ionic selectivity including those selective for sodium ($Na^+$), potassium ($K^+$), calcium ($Ca^{2+}$), and others. The largest subclass is $K^+$ channels, which are expressed in every tissue in the body where they participate in control of excitability of neurons, muscles, endocrine glands, and the heart while in organs like the kidney they play critical roles in the formation of urine and maintenance of proper $Na^+/K^+$ homeostasis. $K^+$ channel activity can be modulated by changes in transmembrane potential as well as a wide variety of extracellular and intracellular factors including but not limited to: $Ca^{2+}$, membrane lipids, G-protein-coupled receptors, protein kinases, and ATP. A rapidly expanding number of mutations are being identified in $K^+$ channels which can result in neurological, cardiovascular, renal, neoplastic, and metabolic diseases. Although $K^+$ channels have been the target of therapeutic agents, the vast majority of $K^+$ channels do not have potent and selective pharmacological modulators to advance the understanding of their physiological roles or to provide a foundation for developing $K^+$ channel-targeted medicines. Thus, there is a desperate need to discover and characterize new $K^+$ channel modulators, as well as robust chemical tools to study the $K^+$ channels.

High-throughput screening (HTS) is an important method for the discovery of $K^+$ channel modulators by enabling the rapid testing of thousands-to-millions of molecules to identify those with activity against the channel of interest. Success in screening depends on the development of robust, HTS-compatible assays capable of detecting subtle changes in channel activity. Electrophysiology is the most sensitive technique for assaying ion channel activity, though HTS-compatible electrophysiology technologies currently suffers from some drawbacks including high cost and lack of versatility, such as its requirement to dissociate cells from their growth substrate. An alternate approach is the use of ion flux assays where channel activity is monitored by the increase or decrease in fluorescence of an ion-sensing dye as a measure of passage of that ion through the channel of interest. In particular, the thallium ($Tl^+$) flux assay is highly compatible with kinetic imaging-based HTS assays. In addition, $Tl^+$ flux assays are >5-fold cheaper per well than HTS-compatible electrophysiology assays (largely due to plate cost). $Tl^+$ flux has been used in numerous HTS campaigns to identify modulators of $K^+$ channels implicated in disease and have also been used to screen compounds for activity against $K^+$ transporters, $Na^+$ channels, and non-selective cation channels.

$Tl^+$ flux assays utilize the ability of $Tl^+$ to pass through numerous $K^+$ channels coupled with a cell-permeable fluorescent $Tl^+$ indicator (a representative scheme is shown FIG. 1). Several fluorescent $Tl^+$ indicators have been reported with the most robust, such as Thallos (1), consisting of a fluorescein moiety coupled to an amino dicarboxylic acid metal binding unit. The fluorescence pathway is partially quenched in the non-$Tl^+$ bound form by a presumed photoinduced electron transfer (PET) between the metal-binding unit and fluorophore. When $Tl^+$ is bound, the PET-pathway is inhibited resulting in a higher fluorescence quantum yield for the complex which is observed as a $Tl^+$ concentration dependent increase in fluorescence.

Fluorescein-based metal sensors have found great utility in biology as imaging agents and components of activity assays owing to their high molar absorptivity, large fluorescence quantum yield, and general biocompatibility. However, there are drawbacks to their use including relatively short excitation wavelengths and an undesirable pH sensitivity in the physiological range leading to decreased brightness at lower pH. The short excitation wavelength is particularly a problem in HTS assays since many compound libraries contain molecules with comparable excitation and emission spectra which interfere with the assay. The number of compounds in a library generating this kind of interference tends to decrease as the excitation wavelength increases. Rhodamines, which are red-shifted ~50 nm relative to fluorescein and exhibit excellent pH tolerance, have also been used as the fluorescent components of metal sensors, but have also been shown to accumulate in the mitochondria which is generally undesirable in flux assays. Rhodols are a hybrid of fluorescein and rhodamines exhibiting excitation and emission spectra ~30 nm red-shifted from fluorescein, excellent pH tolerance in the physiological range, and predominantly cytoplasmic accumulation. Rhodol-based "turn-on" metal sensors have been reported for several transition metals including $Hg^{2+}$, $Ag^+$, $Cu^+$ and $Au^{3+}$. PET-based metal sensors utilizing rhodol fluorophores have been reported for imaging $Cu^+$ and $Ca^{2+}$.

There remains a need for novel metal ion sensing compounds for use in HTS assays of $K^+$ channel and other $Tl^+$ conducting systems, particularly those with more red-shifted fluorescence property and/or less pH-sensitivity as compared to the known compounds.

SUMMARY

The present invention provides compounds of formula (I), or a salt thereof,

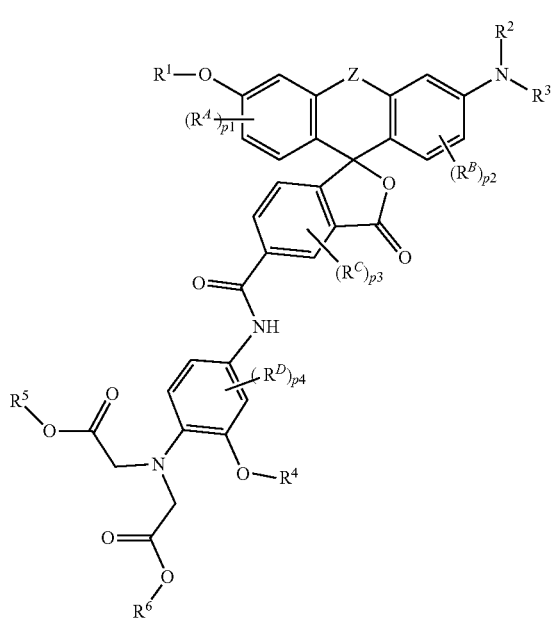

(I)

wherein:

Z is O, $CR^xR^y$, $SiR^xR^y$, or $SO_2$;

$R^1$ is $C_{1-10}$alkyl-CO—;

$R^2$ and $R^3$ are each independently hydrogen, $C_{1-10}$alkyl, $C_{1-10}$alkyl-CO—, —$C_{1-4}$alkylene-$C_{3-10}$cycloalkyl, $C_{3-10}$cycloalkyl, —$C_{1-4}$alkylene-$C_{6-20}$aryl, or $C_{6-20}$aryl, wherein the $C_{1-10}$alkyl; $C_{1-10}$alkyl-CO—; —$C_{1-4}$alkylene-$C_{3-10}$cycloalkyl, $C_{3-10}$cycloalkyl, —$C_{1-4}$alkylene-$C_{6-20}$aryl, and $C_{6-20}$aryl are optionally substituted with one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—;

$R^2$ and $R^3$ together with the N atom they are attached to form a 4 to 8-membered heterocycle, wherein the heterocycle is optionally substituted one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—;

$R^4$ is $C_{1-10}$alkyl;

$R^5$ and $R^6$ are each independently $C_{1-6}$alkyl, —$C_{1-4}$-alkylene-O—$R^z$, —$C_{1-4}$-alkylene-O—CO—$R^z$, or —$C_{1-4}$-alkylene-O—C(O)—O—$R^z$;

$R^A$, $R^B$, $R^C$, and $R^D$ are each independently selected from the group consisting of halogen, $C_{1-4}$haloalkyl, —CN, $C_{1-4}$alkyl-, $C_{1-4}$alkyl-O—, $C_{1-4}$alkyl-CO—NH—, and $C_{1-4}$alkyl-NH—CO—;

p1, p2, p3, and p4 are each independently 0, 1, 2, or 3;

$R^x$ and $R^y$ are each independently $C_{1-4}$alkyl; and $R^z$, at each occurrence, is independently $C_{1-6}$alkyl, $C_{3-10}$cycloalkyl, $C_{6-20}$aryl, or a 4 to 8-membered heterocycle, wherein the $C_{3-10}$cycloalkyl, $C_{6-20}$aryl, and 4 to 8-membered heterocycle are optionally substituted with one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—.

Also provided are methods for preparing compounds of formula (I).

Also provided are methods of using compounds of formula (I) for detecting of the flux of a metal ion, such as $Tl^+$, into a cell.

BRIEF DESCRIPTION OF THE DRAWINGS

FIG. 3A shows fluorescence intensity data from each well were normalized to the averaged fluorescence intensity of the first 6 time points of the experiment and the normalized fluorescence data for each replicate time point were averaged (n=12). FIG. 3B shows the concentration response curve derived from data in (a) by subtracting the vehicle control from each concentration series and sampling a time point several seconds after addition of $Tl^+$ stimulus.

DETAILED DESCRIPTION

Figure 1:
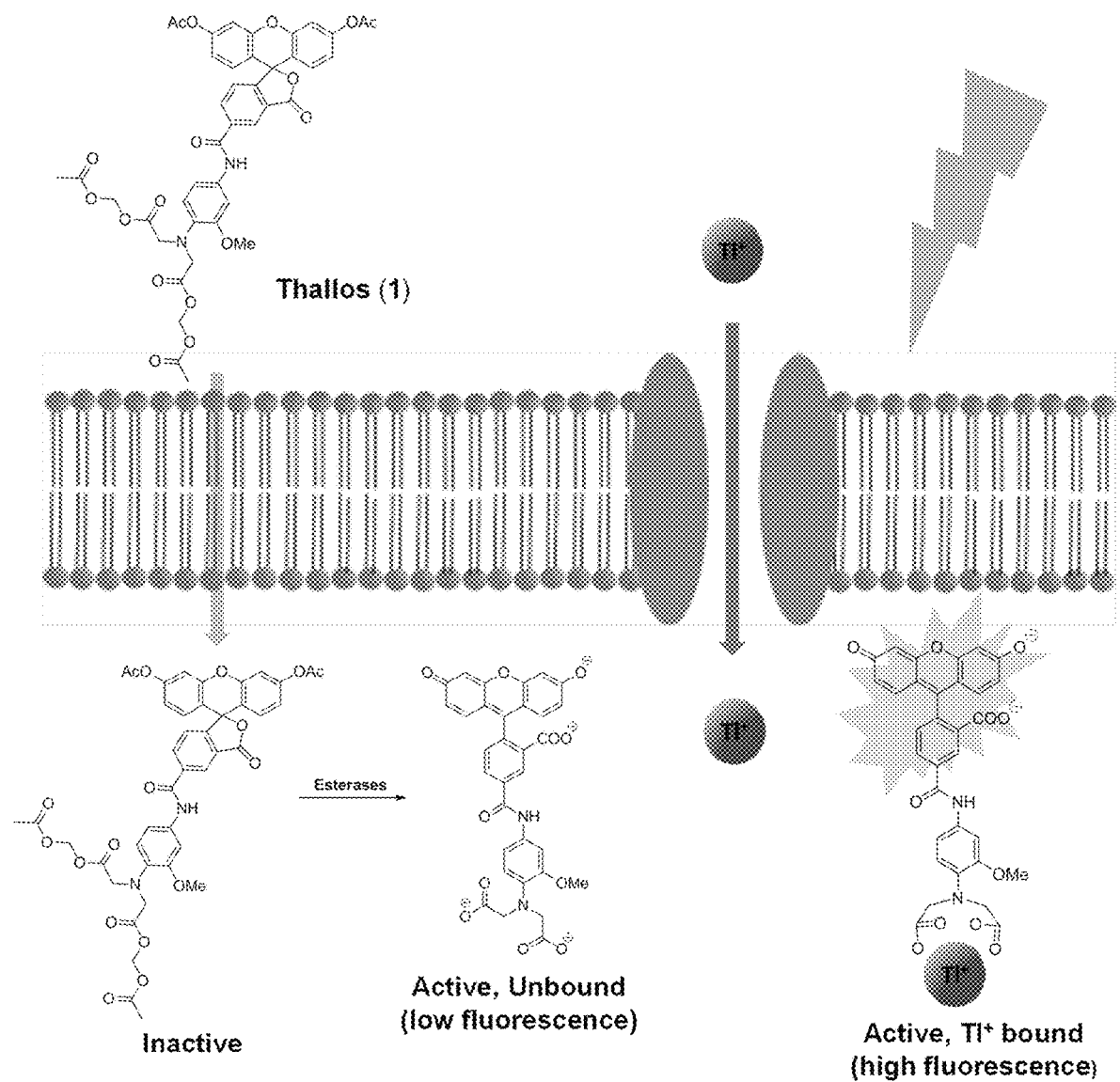
FIG. 1 shows an overview of $Tl^+$ flux assay.

Thallium ($Tl^+$) flux assays are high-throughput screening compatible assays used for the identification of small molecule modulators of potassium (K$^+$) channel activity. The assays exploit the permeability of K$^+$ channels to Tl$^+$ coupled with a cell permeable, fluorescent Tl$^+$ sensitive dye. Common Tl$^+$ sensing dyes utilize fluorescein as the fluorophore though fluorescein exhibits certain undesirable properties in these assays including pH sensitivity and spectral overlap with some molecules found in screening libraries. To overcome these drawbacks, the replacement of fluorescein with rhodols was investigated. A library of 13 rhodol-based Tl$^+$ sensors was synthesized and their properties and performance in Tl$^+$ flux assays evaluated. The dimethyl rhodol Tl$^+$ sensor emerged as the best of the series and performed comparably to fluorescein-based sensors while demonstrating greater pH tolerance in the physiological range and excitation and emission spectra 30 nm red-shifted from fluorescein.

1. Definitions

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched chain saturated hydrocarbon. Representative examples of alkyl include, but are not limited to, methyl, ethyl, npropyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and CH$_2$CH(CH$_3$)CH(CH$_3$)CH$_2$—.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "cycloalkyl" as used herein, means a monovalent group derived from an all-carbon ring system containing zero heteroatoms as ring atoms, and zero double bonds. The all-carbon ring system can be a monocyclic, bicyclic, or tricyclic ring system, and can be a fused ring system, a bridged ring system, or a spiro ring system, or combinations thereof. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic, bicyclic, or tricyclic ring system, and can be a fused ring system, a bridged ring system, or a spiro ring system, or combinations thereof. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and spiro heterocycle groups are connected to the parent molecular moiety through any substitutable carbon atom or any substitutable nitrogen atom contained within the group.

The term "oxo" as used herein refers to an oxygen atom bonded to the parent molecular moiety. An oxo may be attached to a carbon atom or a sulfur atom by a double bond. Alternatively, an oxo may be attached to a nitrogen atom by a single bond, i.e., an N-oxide.

Terms such as "alkyl," "cycloalkyl," "alkylene," etc. may be preceded by a designation indicating the number of atoms present in the group in a particular instance (e.g., "$C_{1\text{-}4}$alkyl," "$C_{3\text{-}6}$cycloalkyl," "$C_{1\text{-}4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1\text{-}4}$," the members of the group that follows may have any number of carbon atoms falling within the recited range. A "$C_{1\text{-}4}$alkyl," for example, is an alkyl group having from 1 to 4 carbon atoms, however arranged (i.e., straight chain or branched).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterioinc forms of the compounds or salts of formula I where appropriate.

2. Compounds

A first aspect of the invention provides compounds of formula (I), or a salt thereof,

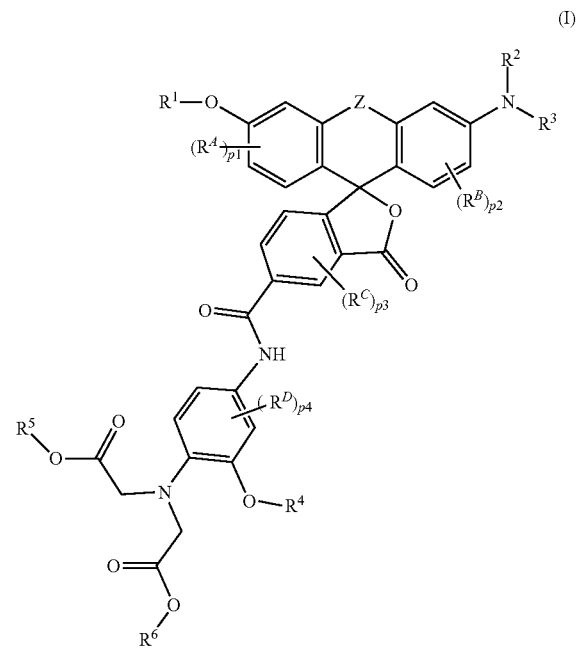

wherein:

Z is O, $CR^xR^y$, $SiR^xR^y$, or $SO_2$;

$R^1$ is $C_{1\text{-}10}$alkyl-CO—;

$R^2$ and $R^3$ are each independently hydrogen, $C_{1\text{-}10}$alkyl, $C_{1\text{-}10}$alkyl-CO—, —$C_{1\text{-}4}$alkylene-$C_{3\text{-}10}$cycloalkyl, $C_{3\text{-}10}$cycloalkyl, —$C_{1\text{-}4}$alkylene-$C_{6\text{-}20}$aryl, or $C_{6\text{-}20}$aryl, wherein the $C_{1\text{-}10}$alkyl; $C_{1\text{-}10}$alkyl-CO—; —$C_{1\text{-}4}$alkylene-$C_{3\text{-}10}$cycloalkyl, $C_{3\text{-}10}$cycloalkyl, —$C_{1\text{-}4}$alkylene-$C_{6\text{-}20}$aryl, and $C_{6\text{-}20}$aryl are optionally substituted with one or more substituents independently selected from the group consisting of halogen, $C_{1\text{-}4}$haloalkyl, —CN, $C_{1\text{-}4}$alkyl-O—, $C_{1\text{-}4}$alkyl-CO—NH—, and $C_{1\text{-}4}$alkyl-NH—CO—; or $R^2$ and $R^3$ together with the N atom they are attached to form a 4 to 8-membered heterocycle, wherein the heterocycle is optionally substituted one or more substituents independently selected from the group consisting of halogen, $C_{1\text{-}4}$haloalkyl, —CN, $C_{1\text{-}4}$alkyl-O—, $C_{1\text{-}4}$alkyl-CO—NH—, and $C_{1\text{-}4}$alkyl-NH—CO—;

$R^4$ is $C_{1\text{-}10}$alkyl;

$R^5$ and $R^6$ are each independently $C_{1\text{-}6}$alkyl, —$C_{1\text{-}4}$-alkylene-O—$R^z$, —$C_{1\text{-}4}$-alkylene-O—CO—$R^z$, or —$C_{1\text{-}4}$-alkylene-O—C(O)—O—$R^z$;

$R^A$, $R^B$, $R^C$, and $R^D$ are each independently selected from the group consisting of halogen, $C_{1-4}$haloalkyl, —CN, $C_{1-4}$alkyl-, $C_{1-4}$alkyl-O—, $C_{1-4}$alkyl-CO—NH—, and $C_{1-4}$alkyl-NH—CO—;

p1, p2, p3, and p4 are each independently 0, 1, 2, or 3;

$R^x$ and $R^y$ are each independently $C_{1-4}$alkyl; and $R^z$, at each occurrence, is independently $C_{1-6}$alkyl, $C_{3-10}$cycloalkyl, $C_{6-20}$aryl, or a 4 to 8-membered heterocycle, wherein the $C_{3-10}$cycloalkyl, $C_{6-20}$aryl, and 4 to 8-membered heterocycle are optionally substituted with one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—.

In some embodiments, Z is O. In some embodiments, Z is $CR^xR^y$, $SiR^xR^y$, or $SO_2$. In some embodiments, Z is $C(CH_3)_2$, $Si(CH_3)_2$, or $SO_2$.

In some embodiments, p1, p2, p3, and p4 are each independently 0 or 1. In some embodiments, p1, p2, p3, and p4 are 0.

In some embodiments, $R^A$, $R^B$, $R^C$, and $R^D$ are each independently halogen, $C_{1-4}$haloalkyl, or —CN. In some embodiments, $R^A$, $R^B$, $R^C$, and $R^D$ are each independently a halogen atom. In some embodiments, $R^A$ is halogen, and p1 is 1. In some embodiments, $R^B$ is halogen, and p2 is 1. In some embodiments, $R^C$ is halogen, and p3 is 1. In some embodiments, $R^D$ is halogen, and p4 is 1.

In some embodiments, $R^1$ is $C_{1-4}$alkyl-CO—. In some embodiments, $R^1$ is $CH_3$—CO—.

In some embodiments, $R^2$ and $R^3$ are each independently hydrogen, $C_{1-10}$alkyl, $C_{1-10}$alkyl-CO—, —$C_{1-4}$alkylene-$C_{3-10}$cycloalkyl, $C_{3-10}$ cycloalkyl, —$C_{1-4}$alkylene-$C_{6-20}$aryl, or $C_{6-20}$aryl, wherein the $C_{1-10}$alkyl, $C_{1-10}$alkyl-CO—, —$C_{1-4}$alkylene-$C_{3-10}$cycloalkyl, $C_{3-10}$cycloalkyl, —$C_{1-4}$alkylene-$C_{6-20}$aryl, and $C_{6-20}$aryl are optionally substituted with one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—.

In some embodiments, $R^2$ and $R^3$ are each independently hydrogen, $C_{1-4}$alkyl, or $C_{3-10}$cycloalkyl (such as cyclohexyl). In some embodiments, $R^2$ and $R^3$ are both hydrogen. In some embodiments, $R^2$ is hydrogen, and $R^3$ is methyl, ethyl, propyl, or butyl. In some embodiments, $R^2$ and $R^3$ are each independently $C_{1-4}$alkyl. In some embodiments, $R^2$ and $R^3$ are both methyl, ethyl, or propyl.

In some embodiments, $R^2$ is hydrogen, and $R^3$ is $C_{3-10}$cycloalkyl. For example, $R^3$ may be a monocyclic $C_{3-10}$cycloalkyl, such as cyclopropyl, cyclobutyl, cyclopentyl, cyclohexyl, cycloheptyl, and cyclooctyl. In some embodiments, $R^2$ is hydrogen, and $R^3$ is cyclohexyl.

In some embodiments, $R^2$ and $R^3$ together with the N atom they are attached to form a 4 to 8-membered heterocycle, wherein the heterocycle is optionally substituted one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—. For example, in some embodiments, the heterocycle is

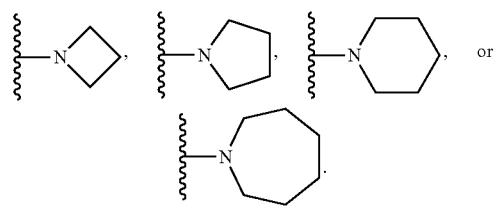

In some embodiments, the heterocycle is not substituted. In some embodiments, the heterocycle is substituted with one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—. In some embodiments, the heterocycle is substituted with 1, 2, 3, 4, or 5 halogen groups. For example, in some embodiments, the heterocycle is

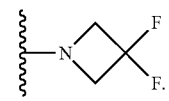

In some embodiments, $R^2$ and $R^3$ together with the N atom they are attached to form a 4 to 8-membered heterocycle, wherein the heterocycle contains at least one heteroatom in addition to the N atom to which $R^2$ and $R^3$ are attached. For example, in some embodiments, the heterocycle is

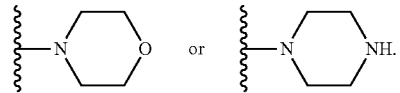

In some embodiments, $R^4$ is $C_{1-4}$alkyl. In some embodiments, $R^4$ is methyl.

In general, $R^5$ and $R^6$ may be cleaved by an esterase to convert the —$OR^5$ and —$OR^6$ groups to —OH. In some embodiments, $R^5$ and $R^6$ have the same structure. In some embodiments, $R^5$ and $R^6$ are independently $C_{1-6}$alkyl, such as methyl, ethyl, propyl, isopropyl, or t-butyl.

In some embodiments, $R^5$ and $R^6$ are independently —$C_{1-4}$-alkylene-O—$R^z$, —$C_{1-4}$-alkylene-O—CO—$R^z$, or —$C_{1-4}$-alkylene-O—C(O)—O—$R^z$. In some embodiments, $R^5$ and $R^6$ are independently —$CH_2$—O—$R^z$, —$CH_2$—O—CO—$R^z$, or —$CH_2$—O—C(O)—O—$R^z$. In some embodiments, $R^5$ and $R^6$ are independently —$CH_2$—O—CO—$R^z$.

In some embodiments, each $R^z$ is independently a $C_{1-6}$alkyl, such as methyl, ethyl, propyl, isopropyl, or t-butyl. In some embodiments, $R^5$ and $R^6$ are —$CH_2$—O—CO—$R^z$, wherein $R^x$ is $C_{1-6}$alkyl. In some embodiments, $R^5$ and $R^6$ are —$CH_2$—O—CO—$CH_3$.

In some embodiments, each $R^z$ is independently $C_{3-10}$cycloalkyl, $C_{6-20}$aryl, or 4 to 8-membered heterocycle, wherein the $C_{3-10}$cycloalkyl, $C_{6-20}$aryl, and 4 to 8-membered heterocycle are optionally substituted with one or more substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—. In some embodiments, each $R^z$ is independently a $C_{3-10}$cycloalkyl, such as cyclopropyl, cyclobutyl, cyclopentyl, cyclohexyl, cycloheptyl, and cyclooctyl, which is unsubstituted or substituted with 1, 2, 3, or 4 substituents independently selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—. In some embodiments, each $R^z$ is independently a $C_{6-20}$aryl, such as phenyl, which is unsubstituted or substituted with 1, 2, 3, or 4 substituents selected from the group consisting of halogen, $C_{1-4}$haloalkyl, —CN, $C_{1-4}$alkyl-O—, $C_{1-4}$alkyl-CO—NH—, and $C_{1-4}$alkyl-NH—CO—.

In some embodiments, the compounds disclosed herein have a structure of formula (I-a), or a salt thereof,

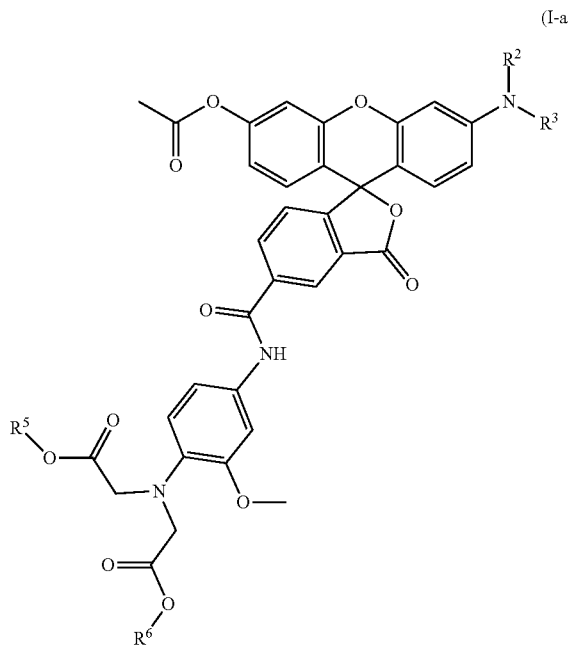

(I-a)

wherein $R^2$, $R^3$, $R^5$, and $R^6$ are as described herein.

In some embodiments, the compound of formula (I) is selected from bis(acetoxymethyl) 2,2'-((4-(3'-acetoxy-6'-amino-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetamido-6'-acetoxy-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(dimethylamino)-3-oxo-3H-spiro[isobenzofuran-1,9'-xanthene]-5-carboxamido)-2-methoxyphenyl)azanediyl)diacetate;

bis(acetoxymethyl) 2,2'-((4-(3'-acetoxy-6'-(diethylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(dipropylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(dibutylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(cyclohexylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(butylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-3-oxo-6'-(phenylamino)-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(azetidin-1-yl)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(3,3-difluoroazetidin-1-yl)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-3-oxo-6'-(pyrrolidin-1-yl)-3H-spiro[isobenzofuran-1,9'-xanthen]-5-ylcarboxamido)-2-methoxyphenyl)azanediyl)diacetate; and bis(acetoxymethyl) 2,2'-((4-(3'-acetoxy-3-oxo-6'-(piperidin-1-yl)-3H-spiro[isobenzofuran-1,9'-xanthen]-5-ylcarboxamido)-2-methoxyphenyl)azanediyl)diacetate, or a salt thereof.

In another embodiment, the compounds include isotope-labelled forms. An isotope-labelled form of a compound is identical to the compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound by well-known methods include isotopes of hydrogen, carbon, nitrogen, oxygen, fluorine and chlorine, for example $^2$H, $^3$H, $^{13}$C, $^{14}$C, $^{15}$N, $^{18}$O, $^{17}$O, $^{18}$F and $^{36}$Cl.

3. Chemical Synthesis

In another aspect, provided are methods of preparing of compounds of formula (I), or salts thereof. In some embodiments, the method comprises reacting a compound of formula (II)

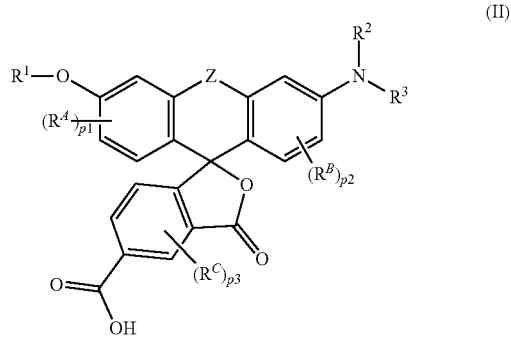

(II)

with a compound of formula (III)

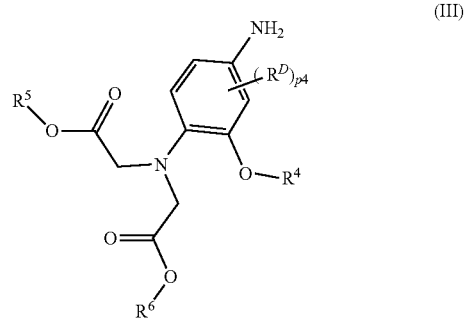

(III)

to the compound of formula (I), wherein Z, $R^1$, $R^2$, $R^3$, $R^4$, $R^5$, $R^6$, $R^A$, $R^B$, $R^C$, $R^D$, p1, p2, p3, and p4 are as described herein.

In some embodiments, the method further comprises converting a compound of formula (IV)

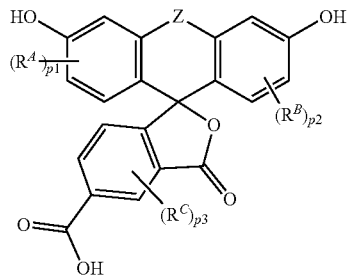

(IV)

to the compound of formula (II), wherein Z, $R^A$, $R^B$, $R^C$, p1, p2, and p3, are as described herein.

In some embodiments, a variable route to the rhodol component of the Tl⁺ sensor was envisioned utilizing a similar strategy as previously described but incorporating protecting groups to allow for orthogonal deprotection of the phenol and distal carboxylic acid functional groups. Scheme 1 shows a representative synthesis route for compounds of formula (I), wherein Z is O.

Scheme 1 Synthesis of rhodol Tl⁺ sensors

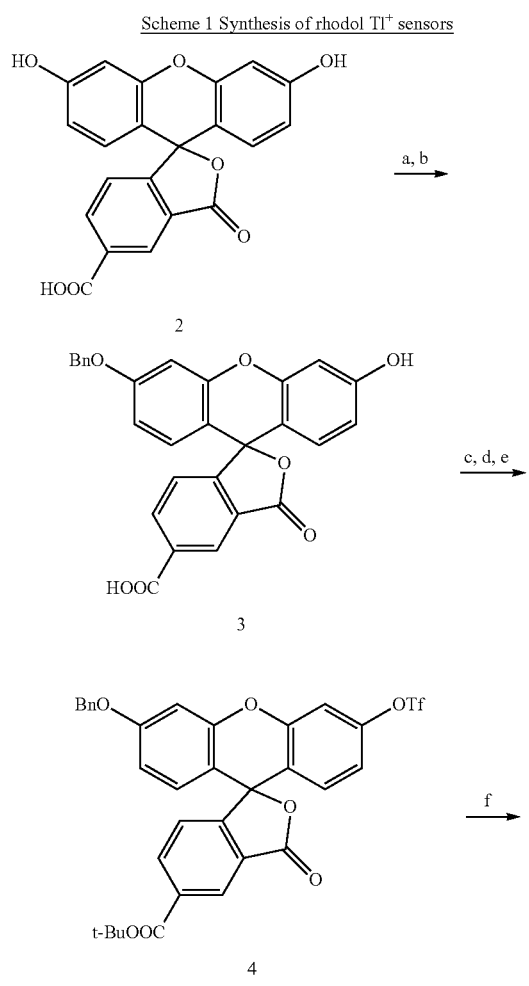

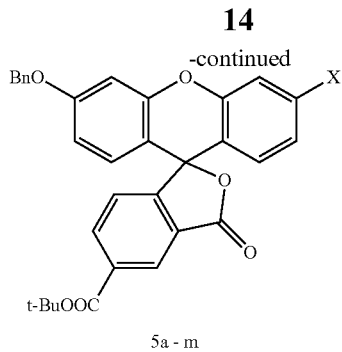

5a - m

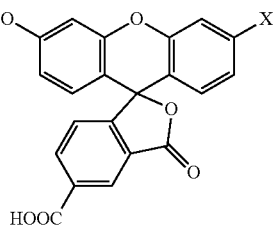

6a - m

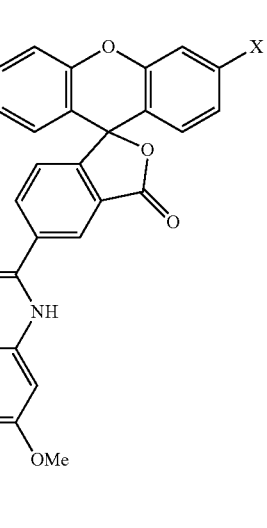

8a - m

R = 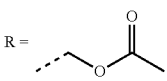

a. BnCl, K₂CO₃, DMF, 120° C., 1 h; b. LiOH, THF/H₂O, 60° C., 1 h, 59% (2 steps);
c. Ac₂O, pyridine, rt, 2 h, d. O-tert-butyldiisopropylisourea, DCM, rt, 48 h, then
NaOMe, MeOH, rt, 20 min, 68% (2 steps), e. Tf₂O, pyridine, DCM, 0° C., 1 h, 78%;
f. amine, PdOAc₂, R-BINAP, Cs₂CO₃, PhMe, 100° C., 20 h, 18-90%; g. H₂, Pd/C,
EtOAc, rt, 1 h; h. TFA, DCM, rt, 12 h; i. Ac₂O, pyridine, rt, 2 h; 22-67% (3 steps);
j. HATU, Et₃N, DMSO, rt, 1 h, 33-58%.

For example, starting from 5-carboxyfluorescein (2), mono-phenol protection as the benzyl ether was accomplished by treatment with benzyl chloride and potassium carbonate in DMF under microwave heating followed by benzyl ester saponification with lithium hydroxide to afford 3. Carboxylic acid 3 was then protected as the t-butyl ester and converted to triflate 4. From this common intermediate, rhodols 5a-m were prepared by Buchwald-Hartwig coupling with the corresponding amine. These compounds were converted to O-acetyl rhodols 6a-m by sequential hydrogenolysis of the benzyl ether, removal of the t-butyl ester by treatment with TFA, and O-acetylation, with the exceptions of 6a, which was O-acetylated prior to t-butyl ester removal and N-Boc deprotection and 6b which was O- and N-acetylated following treatment with TFA. Carboxylic acids 6a-m were coupled to 7 to provide rhodol Tl$^+$ sensors 8a-m (Table 1).

TABLE 1

Photochemical properties of rhodol Tl$^+$ sensors 8a-m. [a, b]

| Compound | X | $\lambda_{max}$ | $\lambda_{em}$ | ε (M$^{-1}$ * cm$^{-1}$) | on/off (Tl$^+$ flux assay) |
|---|---|---|---|---|---|
| 8a | ----NH$_2$ | 496 | 520 | 57000 | 3.02 ± 0.08 |
| 8b | ----NHAc | 463 | NA | 24000 | NA |
| 8c | ----NMe$_2$ | 521 | 551 | 56000 | 4.21 ± 0.04 |
| 8d | ----NEt$_2$ | 525 | 551 | 55000 | 3.28 ± 0.04 |
| 8e | ----NPr$_2$ | 527 | 553 | 66000 | 2.94 ± 0.08 |
| 8f | ----NBu$_2$ | 528 | 556 | 58000 | 1.52 ± 0.01 |
| 8g | ----NH-cyclohexyl | 514 | 535 | 57000 | 4.26 ± 0.07 |
| 8h | ----NHBu | 511 | 533 | 48000 | 3.50 ± 0.07 |
| 8i | ----NHPh | 517 | NA | 52000 | 1.07 ± 0.01 |
| 8j | ----N-azetidinyl | 522 | 550 | 56000 | 3.92 ± 0.13 |
| 8k | ----N-(3,3-difluoroazetidinyl) | 506 | 530 | 66000 | 2.02 ± 0.04 |
| 8l | ----N-pyrrolidinyl | 525 | 553 | 39000 | 3.54 ± 0.07 |
| 8m | ----N-piperidinyl | 526 | 557 | 48000 | 3.09 ± 0.04 |

[a] Absorption maxima, fluorescence emission maxima (both in nm), and molar absorptivity were measured after saponification of 8a-m and dilution into 150 mM KCl buffered with 10 mM HEPES and supplemented with 50 μM EDTA at pH = 7.22.
[b] In cell on/off ratios were determined using HEK-293 cells co-expressing GIRK1 and GIRK2 treated with 8a-m for 1 h and then subjected to Tl$^+$ stimulus. Values represent the maximum fold increase in fluorescence after Tl$^+$ addition (n = 6).

4. Methods of Use

Disclosed are fluorescent thallium ion sensor compounds having a rhodol fluorophore attached to an amino dicarboxylic acid metal binding moiety. These compounds are also referred to herein as metal sensors or dye molecules. These dye molecules are prepared in the "pro-dye" form, with the rhodol oxygen and the carboxylic acids of the metal binding unit masked by protecting groups. These modifications allow for better cell uptake. The protecting groups may be cleaved by cytoplasmic esterase resulting in the active dye molecules, which produce fluorescence signal upon complexing with the metal ion, such as thallium ion (Tl$^+$). The active dye molecules may yield higher fluorescence signal when complexed with a metal ion (i.e. the "metal-bound" state) than that in the absence of the metal ion (i.e. the "unbound" state). Due to their photophysical properties, the compounds disclosed herein are useful in in vitro and cellular assays for measuring metal flux, such as the flux of thallium ion (Tl$^+$). For example, such measurement may be made based on the initial brightness produced by the active compounds in the absence of the metal ion, and the fold-increase in brightness in the presence of the metal ion.

In one aspect, provided is a method of detecting flux of a metal ion into a cell, the method comprising (a) contacting the cell with a compound as disclosed herein, or a salt thereof;

(b) subsequently contacting the cell with the metal ion; and (c) subsequently measuring the fluorescence produced by the cell.

In some embodiments, the metal ion is Tl$^+$.

Suitable cells as disclosed herein include those known in the art for cellular studies of ion channels, such as HEK-293 cells. In some embodiments, the cell comprises at least one ion channel, such as sodium (Na$^+$), potassium (K$^+$), and calcium (Ca$^{2+}$) and others. In some embodiments, the ion channel comprises a potassium channel, such as a G-protein gated inward rectifying K$^+$ channel (GIRK). In some embodiments, the cell may comprise multiple ion channels. In some embodiments, the method as disclosed herein is carried out in HEK-293 cells co-expressing multiple ion channels, such as GIRK1 and GIRK2.

In some embodiments, the method may further comprise measuring the fluorescence produced by the cell after step (a) and before step (b). For example, the method may comprise measuring the initial fluorescence after contacting a compound disclosed herein with a cell in the absence of the metal ion, and the fluorescence of the cell in the presence of the metal ion. In some embodiments, after contacting a compound disclosed herein with a cell, a ratio (e.g. fold increase) between the fluorescence produced by the cell in the absence of a metal ion and that in the presence of the metal ion may be calculated.

5. Example

Method and Materials
General Chemical Synthesis Methods

All non-aqueous reactions were performed in flame-dried flasks under an atmosphere of argon. Stainless steel syringes were used to transfer air- and moisture-sensitive liquids. Reaction temperatures were controlled using a thermocouple thermometer and analog hotplate stirrer. Reactions were conducted at room temperature (rt, approximately 23° C.) unless otherwise noted. Flash column chromatography was conducted using silica gel 230-400 mesh. Analytical thin-layer chromatography (TLC) was performed on E. Merck silica gel 60 F254 plates and visualized using UV and iodine stain.

Materials

Acetic anhydride, trifluoromethanesulfonic anhydride, and HATU were purchased from Oakwood Products (Estill, S.C.). Diisopropylamine, azetidine hydrochloride, 3,3-difluoroazetidine hydrochloride, and cesium carbonate were purchased from Combi-Blocks (San Diego, Calif.). Pyrrolidine was purchase from Acros. 5-carboxyfluorescein (Hammershøj et al., *European J. Org. Chem.* 2015, 2015, 7301-7309) and O-tert-butyl-di-isopropylisourea (West et al., *Org. Lett.* 2005, 7, 2615-2618) were prepared according to literature procedures. All other solvents and chemicals were purchased from Sigma-Aldrich N,N-dimethylformamide (DMF), dichloromethane, pyridine, toluene (PhMe), triethylamine ($Et_3N$), and dimethylsulfoxide (DMSO) were used as received in a bottle with a Sure/Seal. Trifluoromethanesulfonic anhydride was distilled from $P_2O_5$ prior to use. Deuterated solvents were purchased from Cambridge Isotope Laboratories.

Instrumentation $^1H$ NMR spectra were recorded on Bruker 400 or 600 MHz spectrometers and are reported relative to deuterated solvent signals. Data for $^1H$ NMR spectra are reported as follows: chemical shift (δ ppm), multiplicity (s=singlet, d=doublet, t=triplet, q=quartet, p=pentet, m=multiplet, br=broad, app=apparent), coupling constants (Hz), and integration. $^{13}C$ NMR spectra were recorded on Bruker 100 or 150 MHz spectrometers and are reported relative to deuterated solvent signals. Low resolution mass spectrometry (LRMS) was conducted and recorded on an Agilent Technologies 6130 Quadrupole instrument. Preparative scale HPLC was conducted on a Gilson HPLC machine. Automated flash chromatography was performed on a Teledyne Isco purification system.

Example 1 Compound Synthesis

Synthetic Procedures and Compound Characterization

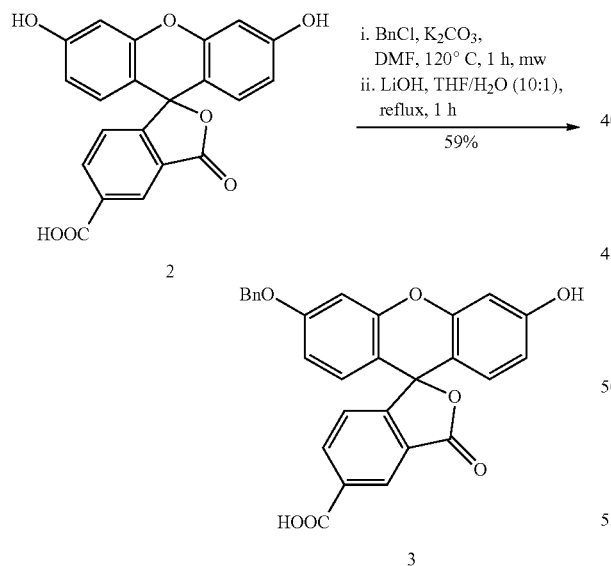

3'-(benzyloxy)-6'-hydroxy-3-oxo-3H-spiro[isobenzofuran-1,9'-xanthene]-5-carboxylic acid (3)

To a stirred solution of 1.35 g (3.59 mmol, 1.0 eq) of 2 in 10 mL of DMF in a 20 mL microwave vial was added 2.48 g (18.0 mmol, 5.0 eq) of $K_2CO_3$ and 1.66 mL (14.4 mmol, 4.0 eq) of benzyl chloride. The vial was capped, flushed with Ar, and maintained at 120° C. under microwave irradiation for 1 h. The reaction was poured into 1 N HCl, the mixture extracted with EtOAc (3×), the organic layers combined and washed with brine, and concentrated. The residue was dissolved in 120 mL of THF and 12 mL of $H_2O$. To this solution was added 431 mg (18.0 mmol, 5.0 eq) of LiOH. The solution was refluxed for 1 h when the reaction was deemed complete by LCMS. The solution was acidified with 1 N HCl and THF removed in vacuo. The resulting mixture was extracted with ethyl acetate (3×), the organic layers were combined, washed with brine, and passed through a phase separator (Biotage). The solution was concentrated and the residue was purified by flash chromatography with hexane and ethyl acetate plus 1% acetic acid to provide 0.99 g (59%) of 3. $^1H$ NMR (400 MHz, acetone-d6) δ 8.56-8.55 (app q, 1H), 8.40 (dd, J=8.02 Hz, J=1.50 Hz, 1H), 7.51-7.47 (m, 2H), 7.43-7.36 (m, 3H), 7.35-7.30 (m, 1H), 6.96-6.95 (app d, 1H), 6.83-6.77 (m, 3H), 6.74 (d, J=8.64 Hz, 1H), 6.65 (dd, J=8.68 Hz, J=2.40 Hz, 1H), 5.20 (s, 2H); $^{13}C$ NMR (100 MHz, acetone-d6) δ 168.6, 166.3, 161.6, 160.5, 157.6, 153.2, 137.7, 137.0, 133.5, 130.2, 130.1, 129.4, 128.8, 128.5, 128.3, 126.8, 125.4, 113.6, 113.4, 112.0, 110.8, 103.4, 102.6, 83.8, 70.8; LRMS calculated for $C_{28}H_{18}O_7$ $[M+H]^+$ m/z: 467.1, measured 467.0.

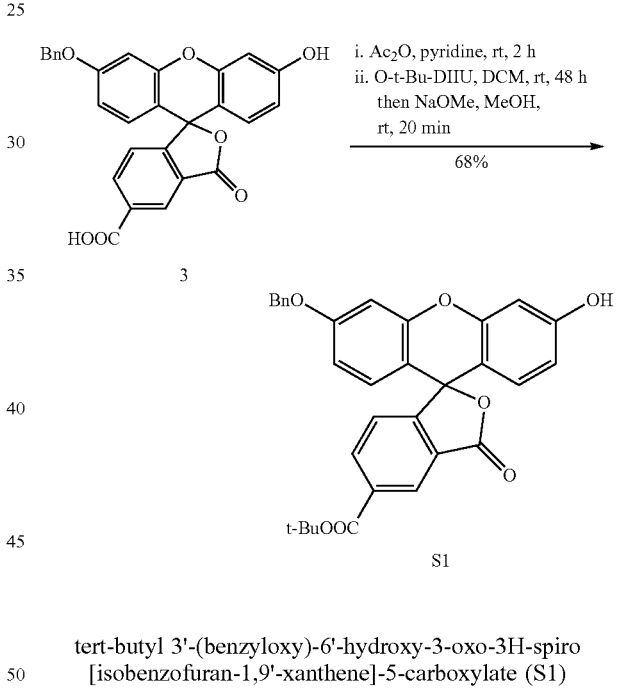

tert-butyl 3'-(benzyloxy)-6'-hydroxy-3-oxo-3H-spiro[isobenzofuran-1,9'-xanthene]-5-carboxylate (S1)

To a stirred solution of 0.49 g (1.05 mmol, 1.0 eq) of 3 in pyridine (5 mL) was added 149 μL (1.58 mmol, 1.5 eq) of acetic anhydride. The solution was stirred at room temperature for 2 h until judged complete by LCMS. The solution was concentrated, the resulting residue acidified with 1 N HCl, extracted with ethyl acetate (3×), washed with brine, and passed through a phase separator (Biotage). The solution was concentrated in vacuo and the residue was dissolved in dichloromethane (5 mL). To this solution was added 630 mg (3.15 mmol, 3.0 eq) of O-t-Bu-DIIU. The solution was stirred for 48 h at room temperature. The resulting suspension was filtered, the solids washed with dichloromethane, the organics combined and concentrated, and the residue dissolved in methanol (5 mL). To this solution was added 1.1 mL (5.25 mmol, 5.0 eq) of 25% sodium methoxide in methanol. The mixture was stirred for 20 min at room temperature, quenched with 1 N HCl, concentrated and extracted with ethyl acetate (3×). The organic layers were combined, washed with brine, passed through a phase separator (Biotage), and concentrated in vacuo. The residue was purified by flash chromatography to provide 0.37 g (68%) of S1. $^1$H NMR (400 MHz, CDCl$_3$) δ 8.62 (s, 1H), 8.29 (dd, J=8.02 Hz, J=1.34 Hz, 1H), 7.44-7.30 (m, 5H), 7.21 (d, J=8.04 Hz, 1H), 6.83 (d, J=2.08 Hz, 1H), 6.74 (d, J=2.00 Hz, 1H), 6.70-6.62 (m, 2H), 6.57-6.50 (m, 2H), 5.07 (s, 2H), 1.64 (s, 9H); $^{13}$C NMR (100 MHz, CDCl$_3$) δ 169.5, 164.4, 160.8, 158.6, 156.6, 152.6, 136.3, 136.2, 134.2, 129.2, 129.1, 128.8, 127.6, 127.1, 126.6, 124.3, 112.7, 112.6, 110.7, 110.3, 103.4, 102.1, 84.7, 82.7, 70.4, 28.3; LRMS calculated for $C_{32}H_{26}O_7$ [M+H]$^+$ m/z: 523.2, measured 523.6.

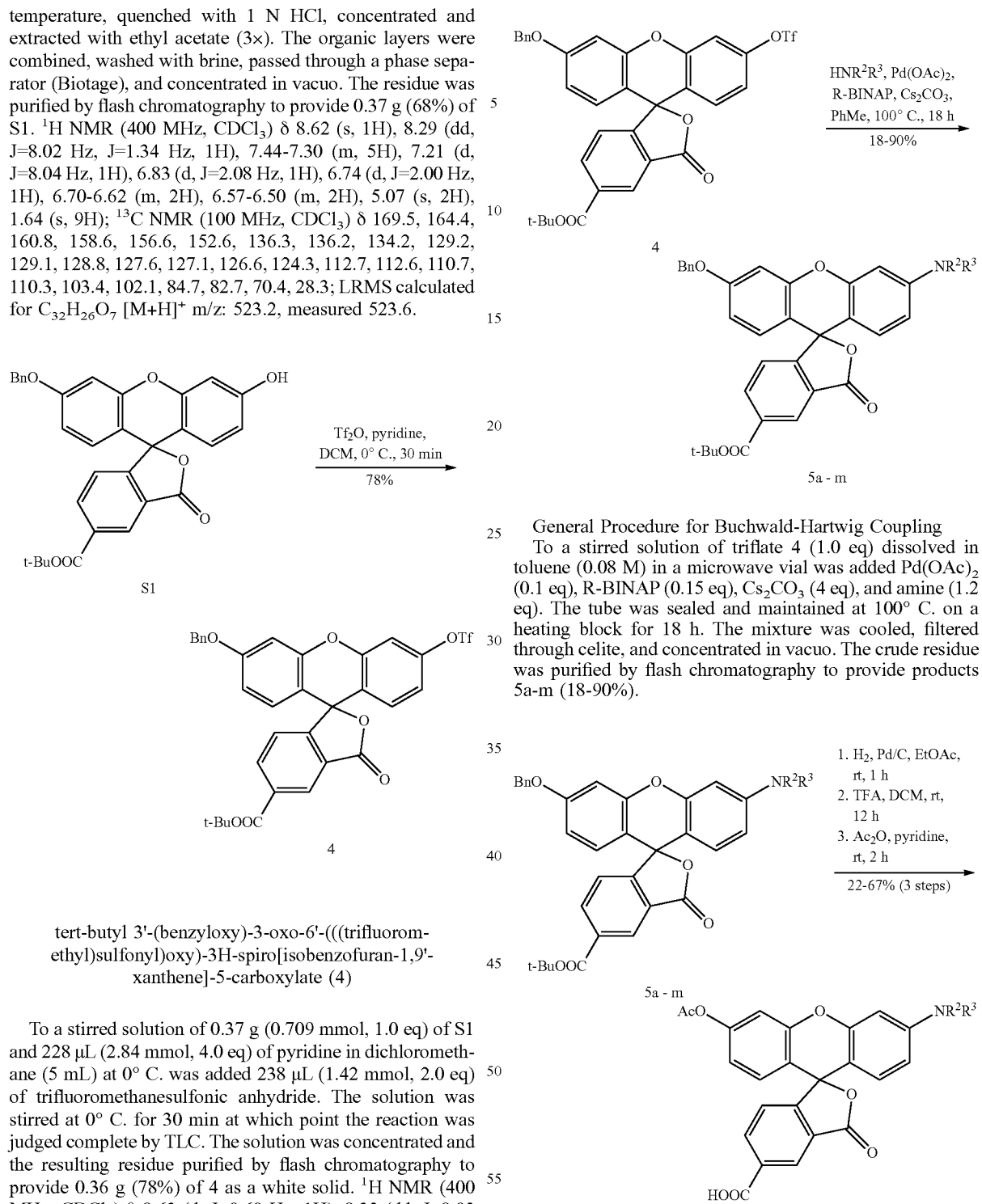

tert-butyl 3'-(benzyloxy)-3-oxo-6'-(((trifluoromethyl)sulfonyl)oxy)-3H-spiro[isobenzofuran-1,9'-xanthene]-5-carboxylate (4)

To a stirred solution of 0.37 g (0.709 mmol, 1.0 eq) of S1 and 228 μL (2.84 mmol, 4.0 eq) of pyridine in dichloromethane (5 mL) at 0° C. was added 238 μL (1.42 mmol, 2.0 eq) of trifluoromethanesulfonic anhydride. The solution was stirred at 0° C. for 30 min at which point the reaction was judged complete by TLC. The solution was concentrated and the resulting residue purified by flash chromatography to provide 0.36 g (78%) of 4 as a white solid. $^1$H NMR (400 MHz, CDCl$_3$) δ 8.63 (d, J=0.60 Hz, 1H), 8.32 (dd, J=8.02 Hz, J=1.42 Hz, 1H), 7.44-7.32 (m, 5H), 7.27-7.25 (m, 1H), 7.22 (d, J=7.88 Hz, 1H), 6.96 (dd, J=8.80 Hz, J=2.40 Hz, 1H), 6.90-6.86 (m, 2H), 6.74 (dd, J=8.84 Hz, J=2.36 Hz, 1H), 6.69 (d, J=8.80 Hz, 1H), 5.10 (s, 2H), 1.64 (s, 9H); $^{13}$C NMR (100 MHz, CDCl$_3$) δ 168.3, 164.0, 161.0, 156.0, 152.1, 151.9, 150.2, 136.5, 134.7, 130.1, 129.1, 128.9, 128.4, 127.6, 126.8, 126.7, 124.1, 119.3, 116.9, 113.4, 110.8, 110.3, 102.2, 82.7, 81.8, 70.5, 28.3; $^{19}$F NMR (376 MHz, CDCl$_3$) δ 75.7; LRMS calculated for $C_{33}H_{25}F_3O_9S$ [M+H]+ m/z: 655.1, measured 655.5.

General Procedure for Buchwald-Hartwig Coupling

To a stirred solution of triflate 4 (1.0 eq) dissolved in toluene (0.08 M) in a microwave vial was added Pd(OAc)$_2$ (0.1 eq), R-BINAP (0.15 eq), Cs$_2$CO$_3$ (4 eq), and amine (1.2 eq). The tube was sealed and maintained at 100° C. on a heating block for 18 h. The mixture was cooled, filtered through celite, and concentrated in vacuo. The crude residue was purified by flash chromatography to provide products 5a-m (18-90%).

General Hydrogenolysis Procedure

To a stirred solution of benzyl ether (1.0 eq) in ethyl acetate (1 mL) was added 10% palladium on carbon (0.05 mol % of palladium). The solution was flushed with Ar and then H$_2$. The reaction was vigorously stirred at room temperature under an atmosphere of H$_2$ until it was judged complete by LCMS (~1 h). The reaction was flushed with Ar, filtered through celite, and concentrated to provide crude phenol. The material was carried on crude to the next step.

General Procedure for t-Butyl Ester Deprotection

To a suspension of phenol (1.0 eq) in DCM (2.0 mL) was added TFA (400 µL). The resulting solution was stirred overnight at room temperature. The reaction was judged complete by LCMS and concentrated. The product was concentrated and carried on crude to the next step.

General O-Acetylation Procedure

To a solution of phenol in pyridine (1.0 mL) was added acetic anhydride (1.5 eq). The solution was stirred until judged complete by LCMS. The solution was concentrated, dissolved in DMSO, and purified by preparative scale reverse phase HPLC using an acetonitrile and water with 0.1% TFA gradient. Fractions containing product were lyophilized to provide 6a-m (22-67%).

Synthesis of 6a and 6b.

The common intermediate for the synthesis of 6a and 6b was prepared by Buchwald-Hartwig coupling of 4 with N-tert-butylcarbamate followed by hydrogenolysis of the benzyl ether as described above. 6a was prepared by O-acetylation followed by ester and N-boc deprotection under the t-butyl ester deprotection conditions described. 6b was prepared first by ester and N-boc deprotection followed by bis-acetylation accomplished by increasing the amount of acetic anhydride in the above O-acetylation conditions to 3 equivalents.

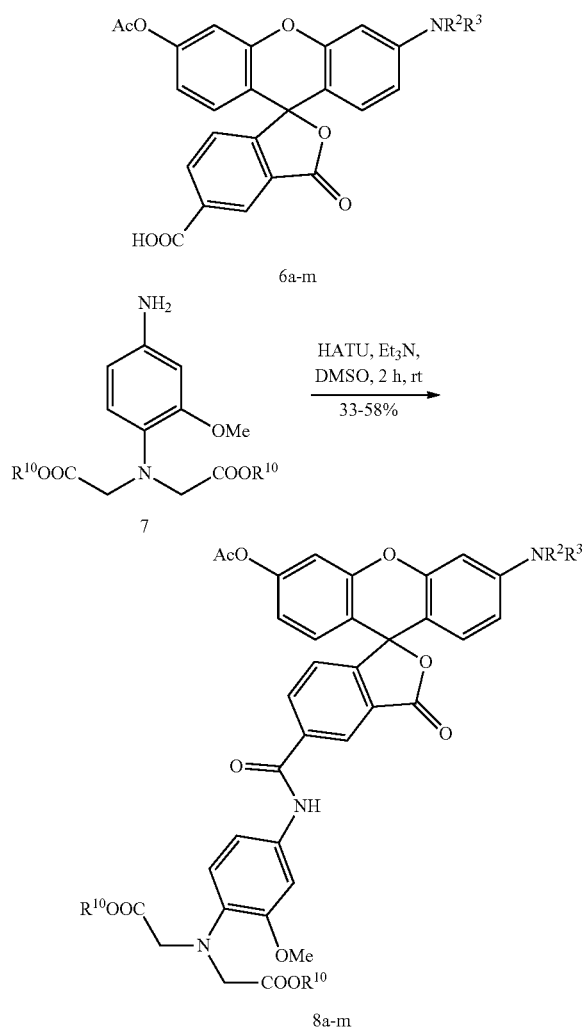

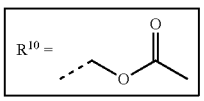

General Coupling Procedure

To a stirred solution of 6a-m in DMSO was added HATU (1.5 eq), triethylamine (2 eq), and 7 (C. D. Weaver, *Thallium Fluorescent Ion Indicator and Assay*, 2015, U.S. Pat. No. 9,103,791 B1) (1.1 eq). The solution was stirred until judged complete by LCMS (1-2 h). The product was purified by preparative reverse phase HPLC using an acetonitrile and water with 0.1% TFA gradient. Fractions containing product were lyophilized to provide 8a-m (33-58%).

Compound Storage

Compounds 8a-m were dissolved in DMSO and stored as 10 mM stock solutions at −20° C. These conditions were generally well tolerated with the exception of 8a which appeared to undergo transacetylation and equilibrated to a mixture of 8a, 8b, and mono-deacetylated species upon storage. To prevent this, dry aliquots of 8a were prepared and dissolved in DMSO immediately before use.

bis(acetoxymethyl) 2,2'-((4-(3'-acetoxy-6'-amino-3-oxo-3H-spiro[isobenzofuran-1,9'-xanthen]-5-ylcarboxamido)-2-methoxyphenyl)azanediyl)diacetate (8a)

$^1$H NMR (600 MHz, CD$_3$CN) δ 8.93 (s, 1H), 8.60 (s, 1H), 8.29 (d, J=7.80 Hz, 1H), 7.44 (s, 1H), 7.40 (d, J=7.86 Hz, 1H), 7.25 (s, 1H), 7.20 (d, J=8.04 Hz, 1H), 7.01 (d, J=8.64 Hz, 1H), 6.95 (d, J=8.16 Hz, 1H), 6.83 (d, J=8.58 Hz, 1H), 6.78 (d, J=8.58 Hz, 1H), 6.65 (s, 1H), 6.59 (d, J=8.34 Hz, 1H), 5.71 (s, 4H), 4.13 (s, 4H), 3.80 (s, 3H), 2.28 (s, 3H), 2.07 (s, 6H); $^{13}$C NMR (150 MHz, CD$_3$CN) δ 171.1, 170.5, 170.0, 168.5, 164.8, 155.5, 154.9, 153.6, 152.2, 138.2, 135.9, 134.9, 134.4, 131.2, 130.5, 129.0, 127.1, 126.6, 119.9, 119.8, 115.6, 113.9, 111.5, 106.7, 100.6, 80.1, 56.3, 54.4, 21.3, 20.9; LRMS calculated for C$_{40}$H$_{35}$N$_3$O$_{15}$ [M+H]$^+$ m/z: 798.2; measured 798.4.

bis(acetoxymethyl) 2,2'-((4-(3'-acetamido-6'-acetoxy-3-oxo-3H-spiro[isobenzofuran-1,9'-xanthen]-5-ylcarboxamido)-2-methoxyphenyl)azanediyl)diacetate (8b)

$^1$H NMR (600 MHz, CD$_3$CN) δ 8.88 (s, 1H), 8.55-8.51 (app d, 2H), 8.27 (dd, J=8.01 Hz, J=1.17 Hz, 1H), 7.82 (d, J=1.62 Hz, 1H), 7.45 (d, J=1.74 Hz, 1H), 7.37 (d, J=8.04 Hz, 1H), 7.19 (dd, J=8.58 Hz, J=2.04 Hz, 1H), 7.15 (d, J=2.16 Hz, 1H), 7.11 (dd, J=8.67 Hz, J=2.01 Hz, 1H), 6.91 (d, J=8.70 Hz, 1H), 6.86 (dd, J=8.64 Hz, J=2.16 Hz, 1H), 6.83 (d, J=8.58 Hz, 1H), 6.80 (d, J=8.64 Hz, 1H), 5.71 (s, 4H), 4.13 (s, 4H), 3.81 (s, 3H), 2.27 (s, 3H), 2.08 (s, 3H), 2.06 (s, 6H); $^{13}$C NMR (150 MHz, CD$_3$CN) δ 171.0, 170.5, 170.1, 169.2, 164.8, 156.3, 153.6, 152.7, 152.3, 152.2, 142.6, 138.4, 135.9, 134.5, 130.1, 129.5, 127.6, 125.3, 124.9, 119.9, 119.1, 117.2, 116.2, 113.84, 113.77, 111.5, 83.0, 80.1, 56.3, 54.4, 24.5, 21.2, 20.9; LRMS calculated for C$_{42}$H$_{37}$N$_3$O$_{16}$ [M+H]$^+$ m/z: 840.2, measured 840.3.

bis(acetoxymethyl) 2,2'-((4-(3'-acetoxy-6'-(dimethylamino)-3-oxo-3H-spiro[isobenzofuran-1,9'-xanthene]-5-carboxamido)-2-methoxyphenyl)azanediyl) diacetate (8c)

$^1$H NMR (600 MHz, acetone-d6) δ 9.76 (s, 1H), 8.55 (s, 1H), 8.40 (d, J=7.98 Hz, 1H), 7.64-7.61 (m, 1H), 7.46 (d, J=8.04 Hz, 1H), 7.38-7.34 (m, 1H), 7.16 (d, J=1.80 Hz, 1H), 6.94-6.88 (m, 2H), 6.86 (d, J=8.58 Hz, 1H), 6.67 (d, J=8.94 Hz, 1H), 6.60-6.55 (m, 2H), 5.78 (s, 4H), 4.19 (s, 4H), 3.83 (s, 3H), 3.02 (s, 6H), 2.29 (s, 3H), 2.07 (s, 6H); $^{13}$C NMR (150 MHz, acetone-d6) δ 170.8, 169.9, 169.4, 168.8, 164.4, 164.3, 156.1, 153.5, 153.4, 153.2, 153.0, 152.2, 138.3, 136.0, 135.5, 134.9, 134.8, 129.9, 129.5, 128.2, 125.3, 124.3, 119.8, 118.6, 117.7, 113.5, 113.4, 111.2, 110.4, 106.5, 106.4, 106.3, 99.0, 79.9, 56.2, 54.4, 40.3, 21.0, 20.6; LRMS calculated for $C_{42}H_{39}N_3O_{15}$ [M+H]$^+$ m/z: 826.3, measured 826.5.

bis(acetoxymethyl) 2,2'-((4-(3'-acetoxy-6'-(diethylamino)-3-oxo-3H-spiro[isobenzofuran-1,9'-xanthen]-5-ylcarboxamido)-2-methoxyphenyl)azanediyl)diacetate (8d)

$^1$H NMR (600 MHz, acetone-d6) δ 9.76 (s, 1H), 8.56 (s, 1H), 8.41 (dd, J=7.95 Hz, J=0.81 Hz, 1H), 7.63 (d, J=1.98 Hz, 1H), 7.49 (d, J=8.04 Hz, 1H), 7.36 (dd, J=8.58 Hz, J=2.10 Hz, 1H), 7.18 (d, J=1.50 Hz, 1H), 6.95-6.89 (m, 2H), 6.86 (d, J=8.58 Hz, 1H), 6.68 (d, J=8.58 Hz, 1H), 6.61-6.57 (m, 2H), 5.78 (s, 4H), 4.20 (s, 4H), 3.83 (s, 3H), 3.48 (q, J=7.02 Hz, 4H), 2.29 (s, 3H), 2.07 (s, 6H), 1.19 (t, J=7.02 Hz, 6H); $^{13}$C NMR (150 MHz, acetone-d6) δ 170.8, 169.9, 169.3, 168.8, 164.4, 155.9, 153.6, 153.4, 153.0, 152.2, 150.9, 138.3, 136.0, 135.5, 134.9, 129.9, 129.8, 128.4, 125.4, 124.4, 119.8, 118.5, 117.8, 113.5, 111.2, 110.0, 106.5, 105.6, 87.3, 79.9, 56.2, 54.4, 45.1, 21.0, 20.6, 12.7; LRMS calculated for $C_{44}H_{43}N_3O_{15}$ [M+H]$^+$ m/z: 854.3, measured 854.5.

bis(acetoxymethyl) 2,2'-((4-(3'-acetoxy-6'-(dipropylamino)-3-oxo-3H-spiro[isobenzofuran-1,9'-xanthen]-5-ylcarboxamido)-2-methoxyphenyl)azanediyl)diacetate (8e)

$^1$H NMR (600 MHz, acetone-d6) δ 9.75 (s, 1H), 8.54 (s, 1H), 8.40 (dd, J=7.98 Hz, J=1.14 Hz, 1H), 7.63 (d, J=2.16 Hz, 1H), 7.47 (d, J=7.98 Hz, 1H), 7.36 (dd, J=8.58 Hz, J=2.22 Hz, 1H), 7.16 (d, J=1.74 Hz, 1H), 6.93-6.88 (m, 2H), 6.86 (d, J=8.58 Hz, 1H), 6.63 (d, J=8.58 Hz, 1H), 6.54-6.51 (m, 2H), 5.78 (s, 4H), 4.20 (s, 4H), 3.83 (s, 3H), 3.36 (t, J=7.68 Hz, 4H), 2.28 (s, 3H), 2.07 (s, 6H), 1.64 (sext, J=7.48 Hz, 4H), 0.94 (t, J=7.38 Hz, 6H); $^{13}$C NMR (150 MHz, acetone-d6) δ 170.8, 170.0, 169.3, 168.8, 164.4, 153.5, 153.4, 153.0, 152.2, 151.3, 138.3, 136.0, 135.5, 134.9, 129.9, 129.6, 128.4, 125.4, 124.3, 119.8, 118.5, 117.8, 113.5, 111.2, 110.1, 106.5, 105.5, 98.3, 79.9, 56.2, 54.4, 53.2, 30.3, 21.0, 20.6, 11.5; LRMS calculated for $C_{46}H_{47}N_3O_{15}$ [M+H]$^+$ m/z: 882.3, measured 882.5.

bis(acetoxymethyl) 2,2'-((4-(3'-acetoxy-6'-(dibutylamino)-3-oxo-3H-spiro[isobenzofuran-1,9'-xanthen]-5-ylcarboxamido)-2-methoxyphenyl)azanediyl)diacetate (8f)

$^1$H NMR (600 MHz, acetone-d6) δ 9.77 (s, 1H), 8.54 (s, 1H), 8.40 (d, J=7.98 Hz, 1H), 7.63 (d, J=2.10 Hz, 1H), 7.47 (d, J=7.98 Hz, 1H), 7.38-7.35 (m, 1H), 7.16 (d, J=1.50 Hz, 1H), 6.92-6.87 (m, 2H), 6.86 (d, J=8.64 Hz, 1H), 6.62 (d, J=8.64 Hz, 1H), 6.54-6.50 (m, 2H), 5.78 (s, 4H), 4.20 (s, 4H), 3.83 (s, 3H), 3.38 (t, J=7.68 Hz, 4H), 2.28 (s, 3H), 2.07 (s, 6H), 1.61 (p, J=7.64 Hz, 4H), 1.38 (sext, J=7.51 Hz, 4H), 0.95 (t, J=7.38 Hz, 6H); $^{13}$C NMR (150 MHz, acetone-d6) δ 170.8, 169.9, 169.3, 168.8, 156.1, 153.5, 153.3, 153.0, 152.2, 151.2, 138.3, 136.0, 135.5, 134.9, 129.9, 129.6, 128.3, 125.4, 124.3, 119.8, 118.5, 117.8, 113.5, 111.2, 110.0, 106.5, 105.3, 98.3, 79.9, 56.2, 54.4, 51.2, 21.0, 20.8, 20.6, 14.2; LRMS calculated for $C_{48}H_{51}N_3O_{15}$ [M+H]$^+$ m/z: 910.3, measured 910.6.

bis(acetoxymethyl) 2,2'-((4-(3'-acetoxy-6'-(cyclohexylamino)-3-oxo-3H-spiro[isobenzofuran-1,9'-xanthen]-5-ylcarboxamido)-2-methoxyphenyl)azanediyl)diacetate (8g)

$^1$H NMR (600 MHz, acetone-d6) δ 9.76 (s, 1H), 8.54 (s, 1H), 8.40 (d, J=7.26 Hz, 1H), 7.62 (d, J=2.10 Hz, 1H), 7.47 (d, J=8.04 Hz, 1H), 7.36 (dd, J=8.58 Hz, J=2.22 Hz, 1H), 7.15 (s, 1H), 6.89 (s, 2H), 6.85 (d, J=8.64 Hz, 1H), 6.55 (d, J=8.70 Hz, 1H), 6.50 (d, J=2.04 Hz, 1H), 6.46 (dd, J=8.73 Hz, J=2.19 Hz, 1H), 5.78 (s, 4H), 4.19 (s, 4H), 3.83 (s, 3H), 3.40-3.43 (m, 2H), 2.28 (s, 3H), 2.07 (s, 6H), 1.80-1.74 (s, 2H), 1.67-1.62 (m, 1H), 1.48-1.39 (m, 2H), 1.31-1.19 (m, 3H); $^{13}$C NMR (150 MHz, acetone-d6) δ 170.8, 169.9, 169.3, 168.8, 153.7, 153.4, 153.0, 152.2, 151.6, 136.0, 135.4, 129.9, 129.6, 128.4, 125.4, 124.4, 119.8, 118.5, 117.8, 113.5, 112.0, 111.2, 106.5, 98.3, 79.9, 56.2, 54.4, 51.9, 33.6, 30.3, 26.6, 25.6, 21.0, 20.5; LRMS calculated for $C_{46}H_{45}N_3O_{15}$ [M+H]$^+$ m/z: 880.3, measured 880.5.

bis(acetoxymethyl) 2,2'-((4-(3'-acetoxy-6'-(butylamino)-3-oxo-3H-spiro[isobenzofuran-1,9'-xanthen]-5-ylcarboxamido)-2-methoxyphenyl)azanediyl)diacetate (8h)

$^1$H NMR (600 MHz, acetone-d6) δ 9.76 (s, 1H), 8.54 (s, 1H), 8.40 (d, J=8.04 Hz, 1H), 7.62 (d, J=1.92 Hz, 1H), 7.47 (d, J=8.04 Hz, 1H), 7.36 (dd, J=8.55 Hz, J=2.07 Hz, 1H), 7.16 (d, J=0.72 Hz, 1H), 6.93-6.88 (m, 2H), 6.86 (d, J=8.58 Hz, 1H), 6.58 (d, J=8.52 Hz, 1H), 6.50-6.46 (m, 2H), 5.78 (s, 4H), 4.20 (s, 4H), 3.83 (s, 3H), 3.19 (t, J=7.05 Hz, 2H), 2.29 (s, 3H), 2.07 (s, 6H), 1.64 (p, J=7.60 Hz, 2H), 1.46 (sext, J=8.28 Hz, 2H), 0.95 (t, J=7.38 Hz, 3H); $^{13}$C NMR (150 MHz, acetone-d6) δ 170.8, 170.0, 169.3, 168.8, 164.4, 153.7, 153.4, 153.0, 152.2, 138.3, 136.0, 135.4, 134.9, 129.9, 128.4, 125.5, 124.4, 119.8, 118.6, 117.8, 113.5, 111.7, 111.2, 106.5, 97.9, 79.9, 56.2, 54.4, 42.6, 31.9, 30.3, 21.0, 20.9, 20.6, 14.1; LRMS calculated for $C_{44}H_{43}N_3O_{15}$ [M+H]$^+$ m/z: 854.3, measured 854.1.

bis(acetoxymethyl) 2,2'-((4-(3'-acetoxy-3-oxo-6'-(phenylamino)-3H-spiro[isobenzofuran-1,9'-xanthen]-5-ylcarboxamido)-2-methoxyphenyl)azanediyl)diacetate (8i)

$^1$H NMR (600 MHz, CD$_3$CN) δ 8.89 (s, 1H), 8.54 (s, 1H), 8.29 (d, J=7.92 Hz, 1H), 7.45 (s, 1H), 7.39 (d, J=7.98 Hz, 1H), 7.35 (t, J=7.83 Hz, 2H), 7.22-7.18 (m, 3H), 7.14 (d, J=2.04 Hz, 1H), 7.06 (t, J=7.35 Hz, 1H), 6.95 (d, J=2.04 Hz, 1H), 6.93 (d, J=8.70 Hz, 1H), 6.88 (dd, J=8.67 Hz, J=2.07 Hz, 1H), 6.83 (d, J=8.58 Hz, 1H), 6.80 (dd, J=8.70 Hz, J=2.01 Hz, 1H), 6.74 (d, J=8.76 Hz, 1H), 5.71 (s, 4H), 4.13 (s, 4H), 3.81 (s, 3H), 2.27 (s, 3H), 2.06 (s, 6H); $^{13}$C NMR (150 MHz, CD$_3$CN) δ 170.5, 170.1, 169.0, 164.8, 153.9, 153.0, 152.2, 142.2, 138.3, 135.9, 135.6, 134.5, 130.5, 130.3, 130.2, 128.2, 125.8, 125.3, 123.8, 120.9, 119.9, 117.7, 114.5, 113.8, 111.5, 106.7, 102.0, 80.1, 56.3, 54.4, 21.3, 20.9; LRMS calculated for $C_{46}H_{39}N_3O_{15}$ [M+H]$^+$ m/z: 874.2, measured 874.4.

bis(acetoxymethyl) 2,2'-((4-(3'-acetoxy-6'-(azetidin-1-yl)-3-oxo-3H-spiro[isobenzofuran-1,9'-xanthen]-5-ylcarboxamido)-2-methoxyphenyl)azanediyl)diacetate (8j)

$^1$H NMR (600 MHz, CD$_3$CN) δ 8.90 (s, 1H), 8.57 (s, 1H), 8.29 (dd, J=8.01 Hz, J=1.47 Hz, 1H), 7.45 (d, J=1.98 Hz,

1H), 7.39 (d, J=7.92 Hz, 1H), 7.22-7.18 (m, 2H), 6.96 (d, J=8.70 Hz, 1H), 6.90 (dd, J=8.70 Hz, J=2.16 Hz, 1H), 6.83 (d, J=8.64 Hz, 1H), 6.76 (d, J=9.36 Hz, 1H), 6.34-6.31 (m, 2H), 5.71 (s, 4H), 4.13 (s, 4H), 4.03 (t, J=7.38 Hz, 4H), 3.81 (s, 3H), 2.41 (p, J=7.38 Hz, 2H), 2.27 (s, 3H), 2.06 (s, 6H); $^{13}$C NMR (150 MHz, CD$_3$CN) δ 171.1, 170.5, 170.1, 168.7, 164.8, 153.3, 152.2, 138.2, 135.9, 135.2, 134.5, 130.5, 130.3, 128.8, 119.9, 119.4, 113.8, 111.5, 106.7, 97.5, 80.1, 56.3, 54.4, 53.2, 21.3, 20.9, 17.1; LRMS calculated for $C_{43}H_{39}N_3O_{15}$ [M+H]$^+$ m/z: 838.2, measured 838.5.

bis(acetoxymethyl) 2,2'-((4-(3'-acetoxy-6'-(3,3-difluoroazetidin-1-yl)-3-oxo-3H-spiro[isobenzofuran-1,9'-xanthen]-5-ylcarboxamido)-2-methoxyphenyl)azanediyl)diacetate (8k)

$^1$H NMR (600 MHz, CD$_3$CN) δ 8.88 (s, 1H), 8.51 (s, 1H), 8.27 (dd, J=8.01 Hz, J=1.17 Hz, 1H), 7.45 (d, J=1.80 Hz, 1H), 7.35 (d, J=8.04 Hz, 1H), 7.19 (dd, J=8.58 Hz, J=2.10 Hz, 1H), 7.12 (d, J=2.16 Hz, 1H), 6.88 (d, J=8.64 Hz, 1H), 6.86-6.82 (m, 2H), 6.72 (d, J=8.64 Hz, 1H), 6.44 (d, J=2.28 Hz, 1H), 6.33 (dd, J=8.64 Hz, J=2.34 Hz, 1H), 5.71 (s, 4H), 4.30 (t, J=12.00 Hz, 4H), 4.13 (s, 4H), 3.81 (s, 3H), 2.26 (s, 3H), 2.06 (s, 6H); $^{13}$C NMR (150 MHz, CD$_3$CN) δ 171.0, 170.5, 170.1, 169.2, 164.8, 156.2, 153.5, 153.0, 152.7, 152.2, 138.3, 135.9, 135.8, 134.5, 130.1, 130.0, 127.9, 125.2, 124.8, 119.9, 119.0, 117.5, 113.8, 111.5, 110.7, 109.1, 106.6, 100.2, 83.8, 80.1, 64.1, 63.9, 63.8, 56.3, 54.4, 21.2. 20.9; LRMS calculated for $C_{43}H_{37}F_2N_3O_{15}$ [M+H]$^+$ m/z: 874.2, measured 874.4.

bis(acetoxymethyl) 2,2'-((4-(3'-acetoxy-3-oxo-6'-(pyrrolidin-1-yl)-3H-spiro[isobenzofuran-1,9'-xanthen]-5-ylcarboxamido)-2-methoxyphenyl)azanediyl)diacetate (8l)

$^1$H NMR (600 MHz, CD$_3$CN) δ 8.92 (s, 1H), 8.53 (s, 1H), 8.27 (dd, J=8.01 Hz, J=1.41 Hz, 1H), 7.45 (dd, J=1.86 Hz, 1H), 7.36 (d, J=7.98 Hz, 1H), 7.20 (dd, J=8.58 Hz, J=2.10 Hz, 1H), 7.14 (d, J=2.16 Hz, 1H), 6.90 (d, J=8.64 Hz, 1H), 6.85 (dd, J=8.67 Hz, J=2.25 Hz, 1H), 6.83 (d, J=8.58 Hz, 1H), 6.68 (d, J=9.42 Hz, 1H), 6.45-6.41 (m, 2H), 5.71 (s, 4H), 4.13 (s, 4H), 3.81 (s, 3H), 3.36-3.34 (m, 4H), 2.27 (s, 3H), 2.06 (s, 6H), 2.03-1.99 (m, 4H); $^{13}$C NMR (150 MHz, CD$_3$CN) δ 169.2, 164.9, 153.8, 153.2, 152.2, 138.2, 135.8, 135.4, 134.6, 130.2, 130.0, 128.5, 125.8, 125.2, 119.9, 118.9, 118.0, 113.8, 111.4, 111.3, 106.7, 98.4, 80.1, 56.3, 54.4, 48.7, 41.3, 26.1, 21.3, 20.9; LRMS calculated for $C_{44}H_{41}N_3O_{15}$ [M+H]$^+$ m/z: 852.3, measured 852.4.

bis(acetoxymethyl) 2,2'-((4-(3'-acetoxy-3-oxo-6'-(piperidin-1-yl)-3H-spiro[isobenzofuran-1,9'-xanthen]-5-ylcarboxamido)-2-methoxyphenyl)azanediyl)diacetate (8m)

$^1$H NMR (600 MHz, acetone-d6) δ 9.76 (s, 1H), 8.55 (s, 1H), 8.40 (d, J=7.86 Hz, 1H), 7.65 (d, J=2.28 Hz, 1H), 7.49-7.46 (m, 1H), 7.38-7.34 (m, 1H), 7.16 (d, J=1.98 Hz, 1H), 6.94-6.88 (m, 2H), 6.87-6.84 (m, 1H), 6.80-6.76 (m, 2H), 6.71-6.67 (m, 1H), 5.78 (app t, 4H), 4.19 (s, 4H), 3.82 (s, 3H), 3.32 (s, 4H), 2.29 (app t, 3H), 2.07 (app t, 6H), 1.69-1.60 (m, 6H); $^{13}$C NMR (150 MHz, acetone-d6) δ 170.8, 169.9, 169.3, 168.8, 164.3, 156.1, 154.6, 153.4, 153.2, 152.9, 152.2, 138.4, 136.0, 135.6, 134.9, 129.9, 129.4, 128.1, 125.3, 124.4, 119.8, 118.6, 117.6, 113.5, 113.3, 111.2, 108.1, 106.5, 106.4, 102.1, 79.9, 56.2, 54.4, 49.7, 30.3, 26.1, 25.0, 21.0, 20.6; LRMS calculated for $C_{45}H_{43}N_3O_{15}$ [M+H]$^+$ m/z: 866.3, measured 866.4.

Example 2 Biological Studies

Determination of Photochemical Properties

Figure 7:
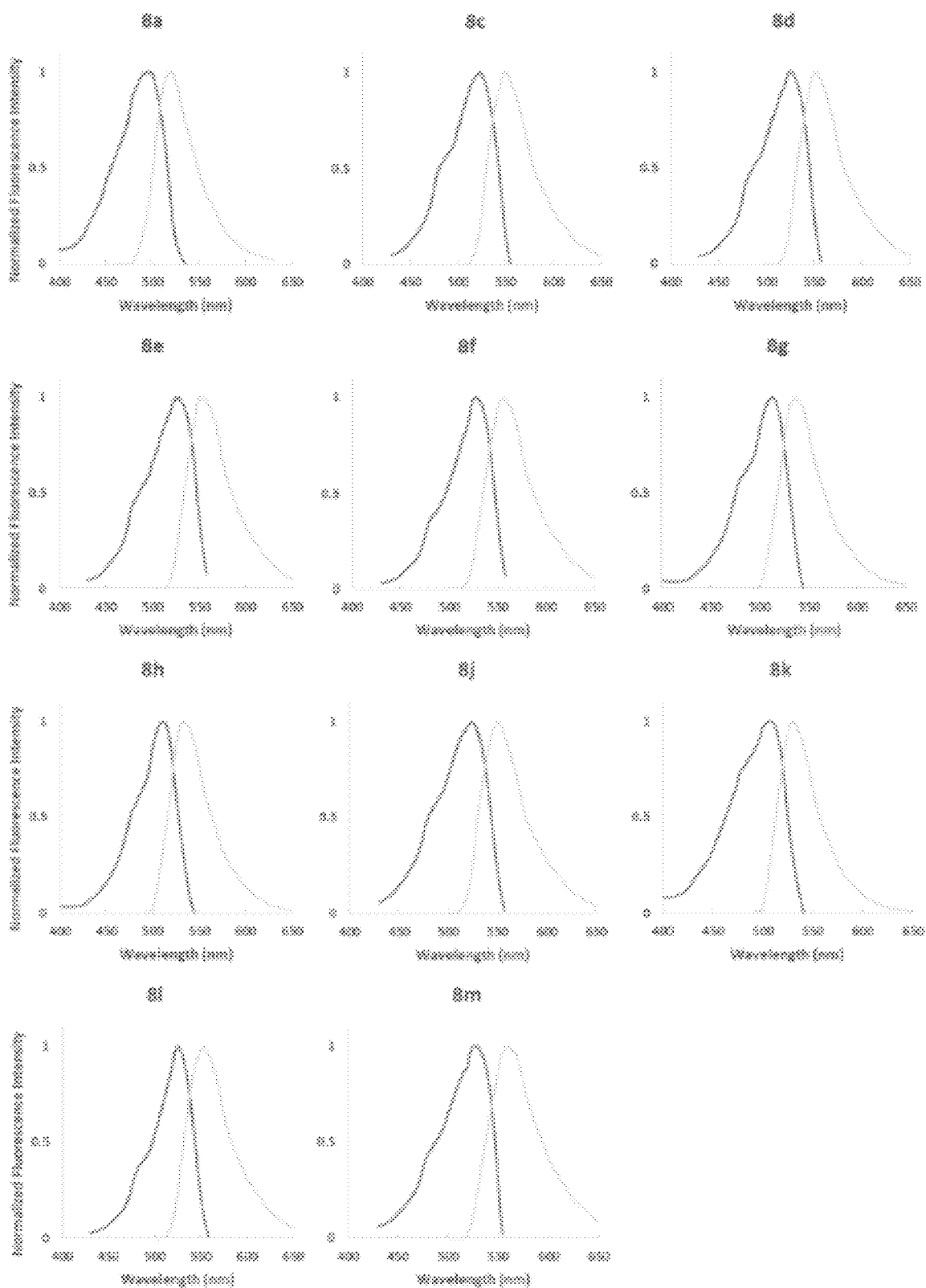
FIG. 7 shows representative excitation and emission spectra of the compounds disclosed herein. Spectra were recorded as described and normalized to the maximum value for each condition.

Evaluation of the photochemical properties of the active Thallium sensing species was accomplished by saponifying 10 μL of each pro-dye stock solution by incubating with 90 μL of 0.1 M KOH for 20 min at 37° C. with the exception of 8b which was treated with 1% NH$_4$OH for 1 h at 37° C. The saponified compounds were diluted into 150 mM KCl buffered with 10 mM HEPES, pH=7.22 with 50 μM of EDTA. All photochemical measurements were taken in this buffer. Absorbance and fluorescence emission spectra were recorded on a Molecular Devices Spectromax M5 using polystyrene cuvettes with path length=1 cm at 23° C. Molar absorptivities are reported for $\lambda_{max}$. The emission wavelengths monitored for recording excitation spectra, the excitation wavelengths used for recording emission spectra, and the corresponding emission cutoff filters used are listed in Table 2 below, and representative excitation and emission spectra are shown in FIG. 7. Spectra for 8b and 8i were not recorded because they exhibit very weak fluorescence.

TABLE 2

| Compounds | Excitation Spectra | | Emission Spectra | |
| --- | --- | --- | --- | --- |
| | Wavelength (nm) | Cutoff (nm) | Wavelength (nm) | Cutoff (nm) |
| 8a | 535 | 530 | 480 | 495 |
| 8g, 8h, 8k | 540 | 530 | 505 | 515 |
| 8c-f, 8j, 8l, 8m | 560 | 550 | 520 | 530 |

Cell Culture

HEK-293 cells co-expressing GIRK1 and GIRK2 were cultured to 80% confluence in a T75 flask (Techno Plastic Products, Trasadingen, CH) at 37° C. and 5% CO$_2$ in medium consisting of Minimal Essential Medium (Cellgro, Manassas, Va.) containing 1× Glutagro (Cellgro, Manassas, Va.) and 10% (v/v) heat-inactivated fetal bovine serum (Life Technologies, Carlsbad, Calif.). The cells were dislodged by treatment with TrypLE (Gibco/Life Technologies, Carlsbad, Calif.), diluted in medium, and plated on clear bottomed, black-walled, amine coated 384 well plates (BD Biosciences, Billerica, Mass.) at a density ~20,000 cells per well. The plated cells were incubated overnight at 37° C. and 5% CO$_2$ and used for the assay the next day.

Fluorescence Microscopy

Figure 2A:
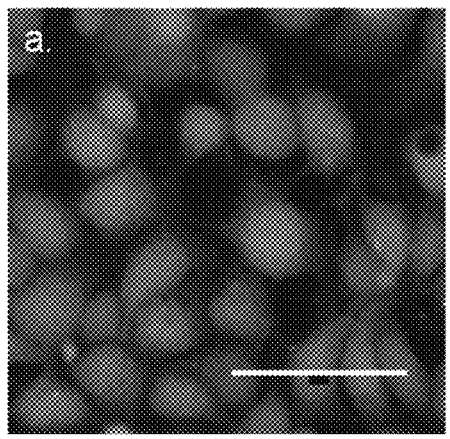
FIG. 2A, FIG. 2B, FIG. 2C, FIG. 2D, FIG. 2E, and FIG. 2F show cellular localization of Thallos (FIGS. 2A, 2C), 8c (FIGS. 2B, 2D), and Rhodamine 123 (FIGS. 2C, 2F). Fluorescence microscopy images were obtained in HEK-293 cells co-expressing GIRK1 and GIRK2 following incubation with Thallos (1 μM), 8c (5 μM), or Rhodamine-123 (1 μM) for 1 h and subsequent counterstaining with Hoechst 33342 (1 μg/mL) (FIGS. 2D-F). Cells were optionally further supplemented with 1 mM of Allura Red AC before imaging (FIGS. 2A-C). Scale bar=50 μm (FIGS. 2A-C) or 10 μm (FIGS. 2D-F). Images were obtained using either a Molecular Devices ImageXpress Micro XL (FIGS. 2A-C) or a Zeiss LSM880 AiryScan with a 40×/1.30 C Plan-Apochromat Oil objective on a 8-well IbiTreat μ-Slide (Ibidi, Madison, Wis.) (FIGS. 2D-F).
Figure 2B:
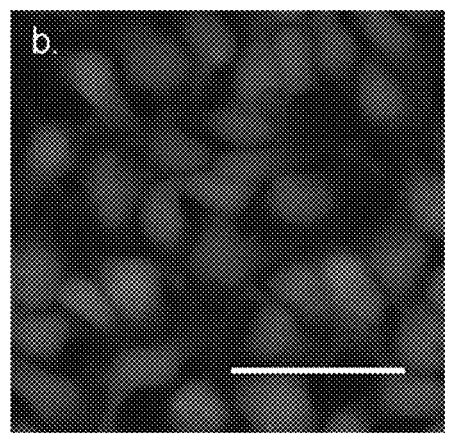
Figure 2C:
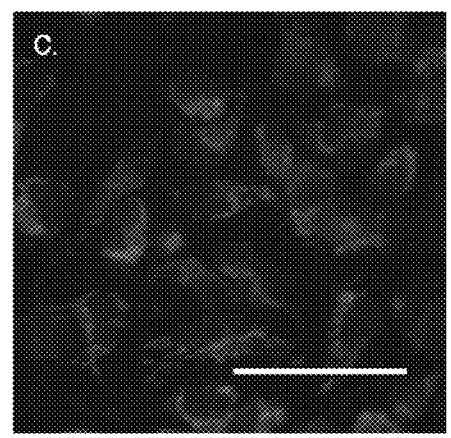

Images were obtained using a Molecular Devices ImageXpress Micro XL. GIRK1 and 2 co-expressing HEK-293 cells were plated in 384-well, clear bottom, black-walled, amine coated plates as described above. Culture medium was replaced by 20 μL of assay buffer (1× HBSS, 4 mM NaHCO$_3$, and 20 mM HEPES, pH=7.3) containing either 1 μM of Thallos, 5 μM of 8c, or 1 μM of rhodamine 123 (Sigma-Aldrich, St. Louis, Mo.). Cells were incubated in the dark for 1 h at room temperature. The dye loading buffer was then replaced with assay buffer with 1 μg/mL of Hoechst 33342 (Life Technologies, Carlsbad, Calif.) and incubated for 15 min at room temperature. The second dye loading buffer was then replaced with 20 μL of assay buffer supplemented with 1 mM of Allura Red AC (Sigma-Aldrich, St. Louis, Mo.). The cells were then imaged with the ImageXpress Micro XL using the 40× objective and FITC filters for Thallos and Rhodamine 123, Cy3 filters for 8c, and DAPI filters for Hoechst 33342. Representative results obtained by this procedure are shown in FIGS. 2A-2C.

Figure 2D:
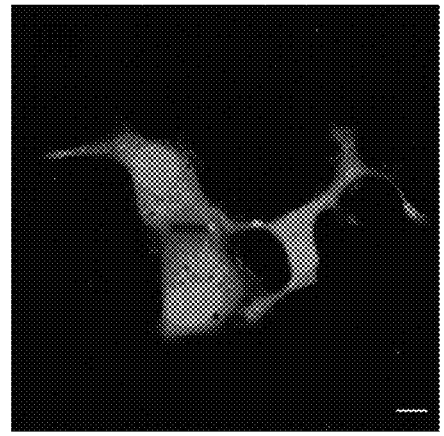
Figure 2E:
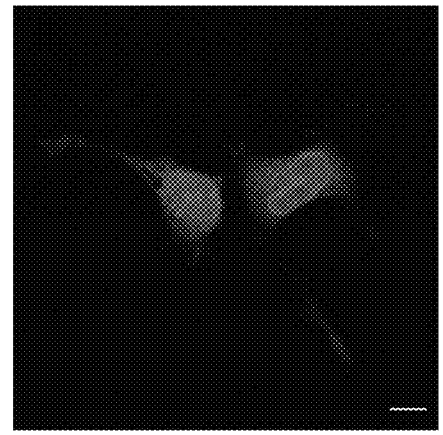
Figure 2F:
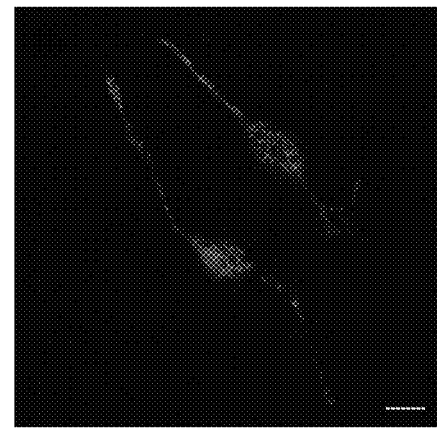

In alternative experiments, HEK cells co-expressing GIRK 1 and GIRK2 were imaged by confocal microscopy using a Zeiss LSM880 AiryScan and a 40×/1.30 C Plan-Apochromat Oil objective on an 8-well IbiTreat µ-Slide (Ibidi, Madison, Wis.). Thallos was imaged using a 488 nm laser and emission collected 493-576 nm, 8c and Rhodamine 123 were imaged using a 514 nm laser and emission collected 519-683 nm, and Hoechst was imaged using a 405 nm laser and emission collected 462-680 nm. Cells were plated on the slide the previous day and culture medium was replaced by 20 µL of assay buffer (1×HBSS, 4 mM $NaHCO_3$, and 20 mM HEPES, pH=7.3) containing either 1 µM of Thallos, 5 µM of 8c, or 1 µM of rhodamine 123 (Sigma-Aldrich, St. Louis, Mo.). Cells were incubated in the dark for 1 h at room temperature. The dye loading buffer was then replaced with assay buffer with 1 µg/mL of Hoechst 33342 (Life Technologies, Carlsbad, Calif.) and incubated for 15 min at room temperature. The second dye loading buffer was then replaced with 20 µL of assay buffer and the cells were imaged. Representative results obtained by this procedure are shown in FIGS. 2D-2F.

Flux Assays—General Procedure

Dye loading—Compounds 8a-m were diluted to a concentration of 5 M in assay buffer (1×HBSS, 4 mM $NaHCO_3$, and 20 mM HEPES, pH=7.3). Dye loading solutions of Thallos were prepared by dissolving a 25 µg aliquot in 30 µL of 6.7% Pluoronic F-127 (w/v) in DMSO and diluting the resulting solution 1:1000 into assay buffer. Culture medium was removed and replaced with 20 µL of dye loading buffer and incubated in the dark at room temperature for 1 h.

Assay—Assays were conducted on a WaveFront Biosciences Panoptic 1 or 2 (WaveFront Biosciences, Franklin, Tenn.) as indicated. Dye loading solutions were removed and replaced with assay buffer immediately before imaging unless otherwise noted. 10 s following commencement of plate imaging, 20 µL of compound at 2.5× concentration in assay buffer was added and incubated for 120 s at which point 10 µL of $Tl^+$ at 5× concentration in stimulus buffer (125 mM $NaHCO_3$, 1.8 mM $CaSO_4$, 1 mM $MgSO_4$, 5 mM glucose, 10 mM HEPES, pH 7.4, and $Tl_2SO_4$), and images taken for the following 120 s.

On/off ratio of 8a-m determined in HEK-293 cells co-expressing GIRK1 and GIRK2—The general $Tl^+$ flux assay procedure outlined above was conducted on a WaveFront Biosciences Panoptic 1 using a checkerboard of 10 µM of ML297 (final concentration) and vehicle. 1 mM of $Tl_2SO_4$ (final concentration) was used for stimulus. Assay and stimulus buffers were supplemented with 2 mM of Allura Red AC. Compounds 8c-m were imaged using 517/20 nm excitation and 562/40 nm emission filters and 8a and 8b were imaged using 480/40 nm excitation and 538/40 nm emission filters (Semrock, Rochester, N.Y.). On/off ratios were calculated by dividing the fluorescence intensity after saturation following $Tl^+$ addition by the fluorescence intensity immediately after compound addition (n=6).

ML297 concentration response curves—In general, all concentration-response data were collected on a WaveFront Biosciences Panoptic 2. Thallos treated cells were imaged using 482/35 nm excitation and 536/40 nm emission filters. 8c treated cells were imaged using 529/24 nm excitation and 565/24 nm emission filters (unless otherwise noted). FluxOR Red treated cells were imaged using 544/24 nm excitation and 593/40 nm emission filters (all filters purchased from Semrock, Rochester, N.Y.). FluxOR Red reagent was prepared according to the manufacturer's procedure. 5 µM of 8c was used for dye loading for all conditions. Dye loading solutions of Thallos were prepared by following the reagent preparation steps listed above and diluting this 1:1000 into the corresponding dye loading buffer.

FluxOR Red procedure with background suppressor. The manufacturer's procedure was followed with the exceptions that the dye loading solution was replaced with 20 µL of assay buffer, solutions of ML297 were prepared in assay buffer plus background suppressor, 20 µL of compound solution was added and 10 µL stimulus buffer (basal) was added according to the general assay protocol described above.

FluxOR Red procedure without background suppressor. The FluxOR Red manufacturer's procedure was followed except the background suppressor was replaced by $H_2O$ in all buffers.

Bicarbonate buffer with Allura Red AC. The assay and stimulus buffers described in the general $Tl^+$ flux procedure were used for dye loading, assay buffer with ML297, and stimulus buffer. All buffers were supplemented with 1 mM of Allura Red AC. The wash step to remove dye loading buffer was omitted.

Bicarbonate buffer without Allura Red AC. The general $Tl^+$ flux procedure was followed without any solutions supplemented with Allura Red AC.

Data from all experiments were processed as follows. The fluorescence intensity values of the first 6 time points for each well were averaged and the fluorescence intensity for all time points in the well was divided by this value to provide $F/F_o$ for each time point. The average $F/F_o$ of the vehicle control was then subtracted from each curve and the normalized, control subtracted fluorescence intensity value was sampled at a time point several seconds after $Tl^+$ addition. These data were averaged (n=6-12 for each concentration of ML297) and fit to a curve using GraphPad Prism. Fold increases in fluorescence reported in the main paper were calculated by averaging $F/F_o$ between 100 and 110 s after $Tl^+$ addition. Data presented in FIG. 3 and FIG. 6 were obtained using 8c with the FluxOR Red kit as described above under the FluxOR Red with background suppressor procedure.

pKa Determination

Saponified 8c and Thallos were prepared and stored as 10 mM solutions in DMSO. These were diluted to 200 µM in DMSO. 5 µL of these solutions were diluted into 195 µL of buffers consisting of 150 mM KCl, 50 µM EDTA, and 10 mM of either potassium citrate (pH=4-6), potassium phosphate (pH=6.25-8), or Tris-HCl (pH=8-9.5) on a 96-well, black walled, clear bottom plate (Greiner Bio-one, Monroe, N.C.). Fluorescence measurements were recorded on a Biotek Neo Synergy plate reader using excitation and emission wavelengths of 485 nm and 528 nm for Thallos and 500 nm and 565 nm for 8c. Fluorescence intensity data were average for each pH (n=3) and the data fit to a curve using GraphPad Prism.

Results

To determine the in vitro photochemical properties of the active $Tl^+$ sensing species, 8a-m were treated with base to remove the acetoxymethyl esters and aryl acetate and then diluted into 10 mM HEPES buffered 150 mM KCl with 50 µM EDTA at pH=7.22. Saponified 8a-m exhibited photochemical properties comparable to previously reported rhodols (Table 1).

The performance of rhodol $Tl^+$ sensors in the $Tl^+$ flux assay was assessed by incubating HEK-293 cells co-expressing G-protein-gated inwardly rectifying $K^+$ (GIRK)

channel subunits GIRK1 and GIRK2 with 8a-m in dye loading buffer for 1 hour prior to addition of 1 mM (final concentration) of $Tl^+$ stimulus and the fold increase in brightness calculated. Dimethyl rhodol 8c demonstrated a 4.21-fold increase in brightness in the presence of $Tl^+$ in HEK-293 cells. A notable decrease in ability to sense $Tl^+$ among the dialkyl series 8c-8f as the alkyl chain length increases was observed. Monoalkyl rhodols 8g and 8h as well as cyclic amine containing rhodols 8j, 8l, and 8m exhibit >3 fold increases in brightness upon addition of $Tl^+$ stimulus. Gem-difluoro 8k exhibited almost half the response to $Tl^+$ compared with the non-fluorinated analog 8j. Phenyl rhodol 8i exhibited very low initial fluorescence in HEK-293 cells requiring a longer exposure time than the other dyes and a minor increase in fluorescence upon addition of $Tl^+$. Fluorescence was not detected in HEK-293 cells incubated with acetamide 8b before or after the addition of $Tl^+$. Considering photochemical properties and response to $Tl^+$ in HEK-293 cells, dimethyl rhodol 8c was identified as the best of the series and further evaluated for its utility as a reagent for $Tl^+$ flux assays.

Cytoplasmic localization of $Tl^+$ indicators is desirable for $Tl^+$ flux assays of ion channels and transporters localized to the plasma membrane. The cellular localization of 8c was compared to Thallos by treating GIRK1 and GIRK2 co-expressing HEK-293 cells with Thallos, 8c, or the mitochondrial stain Rhodamine 123 for 1 h and all counterstained with the nuclear stain Hoechst. Cells were then imaged by fluorescence microscopy. 8c exhibited diffuse cytoplasmic staining comparable to Thallos, in contrast to the punctuate mitochondrial staining observed with Rhodamine 123 (FIGS. 2A-F). These results demonstrate that 8c localizes predominantly to the cytoplasm.

Figure 4:
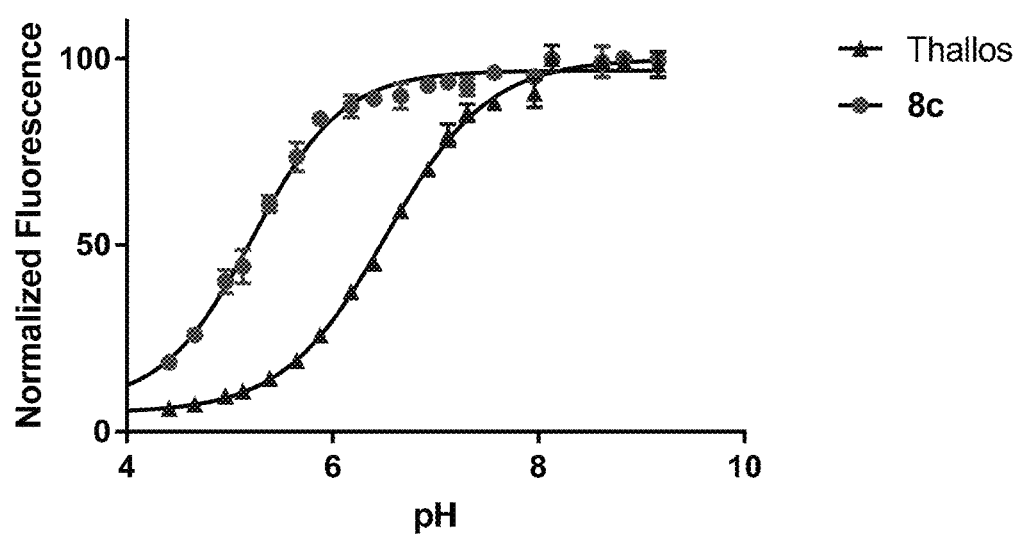
FIG. 4 shows the comparison of pH sensitivity between Thallos and 8c.

The $pK_a$s of 8c and Thallos were determined to be 5.23 and 6.52, respectively (FIG. 4) indicating that 8c may be superior to Thallos when conducting assays at the lower range of physiological pH.

Figure 3A:
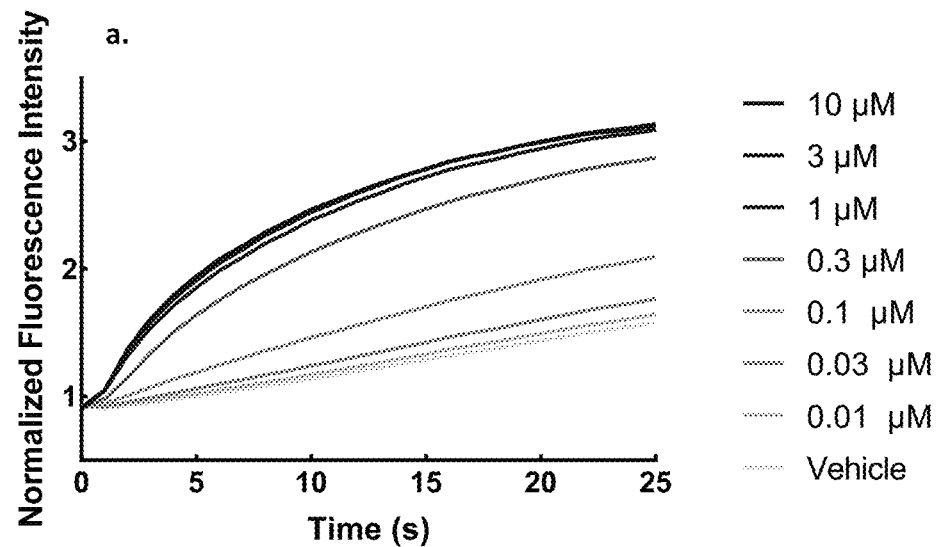
FIG. 3A and FIG. 3B show the concentration response data of ML297 in HEK-293 cells co-expressing GIRK1 and GIRK2 obtained with 8c.
Figure 3B:
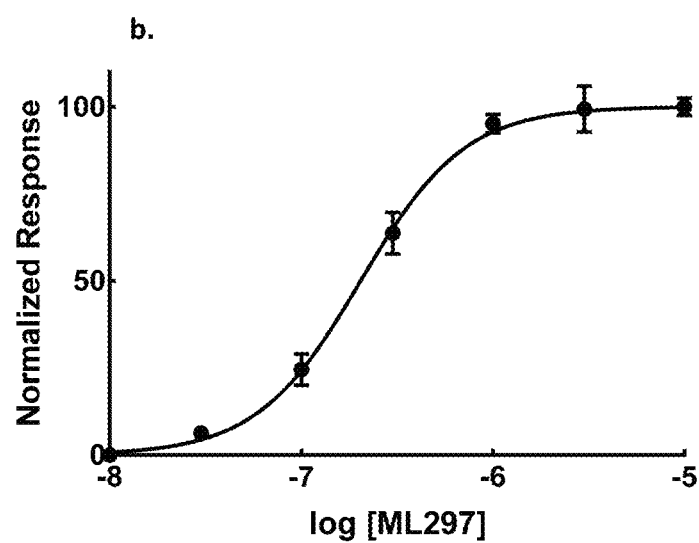

The performance of 8c was evaluated in a $Tl^+$ flux assay to generate a concentration response curve (CRC) of the GIRK activator ML297. HEK-293 cells co-expressing GIRK1 and GIRK2 were loaded with 5 μM of 8c for 1 h, treated with 0.01-10 μM of ML297, and then subjected to $Tl^+$ stimulus (1 mM final concentration). 8c exhibited a 3.09±0.004-fold increase in fluorescence at the highest ML297 concentration (FIG. 3A). Normalized, control subtracted fluorescence intensity values were sampled along the curves following $Tl^+$ addition at each concentration and a CRC was fit using GraphPad Prism (FIG. 3B). The $EC_{50}$ was determined to be 257±3.7 nM while the same procedure utilizing Thallos produced an $EC_{50}$ of 272±23 nM, which was not statistically significantly different.

Figure 5:
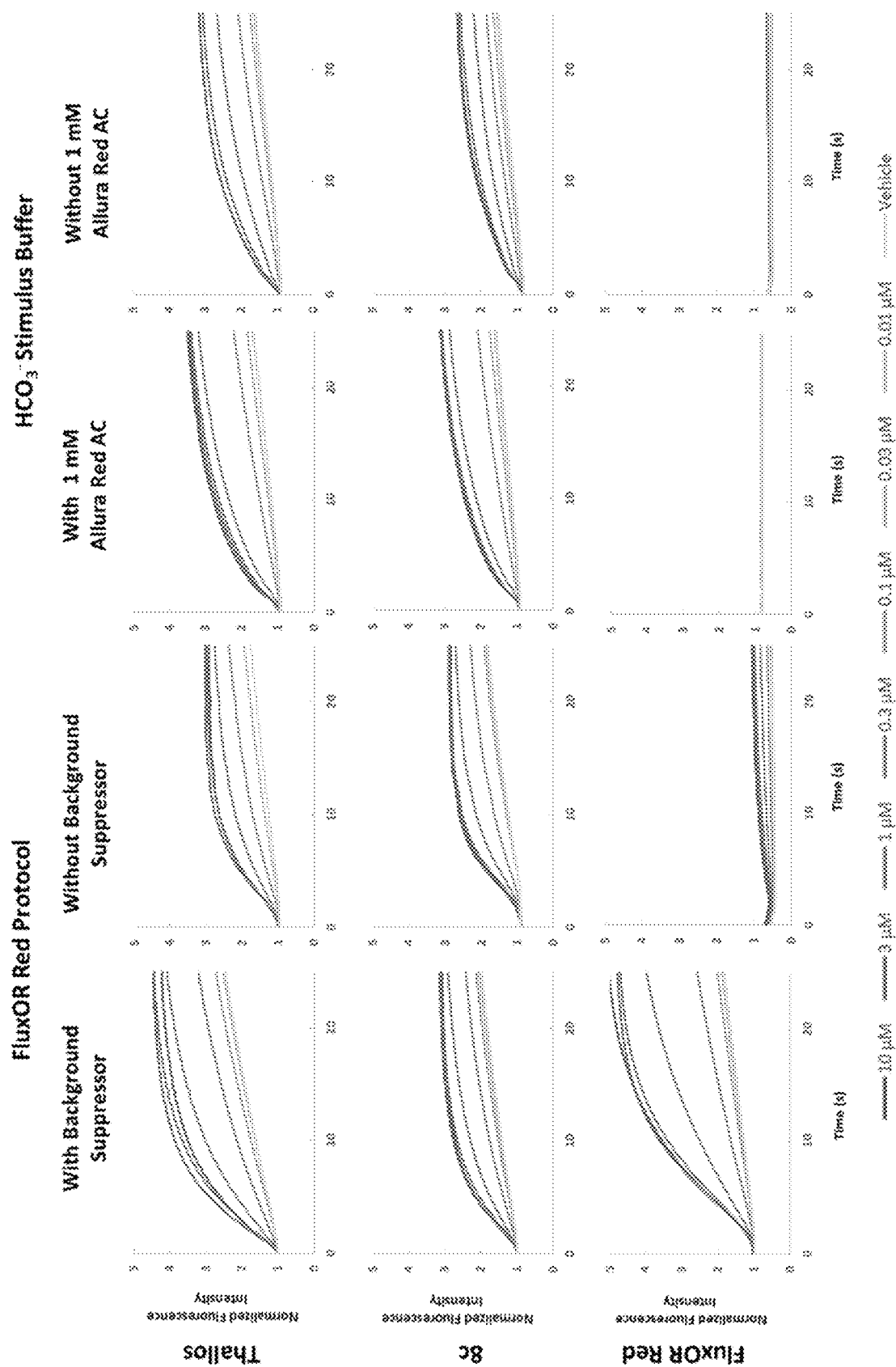
FIG. 5 shows the comparison of dynamic range between Thallos, 8c, and FluxOR Red under the indicated conditions. $Tl^+$ flux assays were conducted in HEK-293 cells co-expressing GIRK1 and GIRK2 and treated with varying concentrations of the GIRK activator ML297. Fluorescence intensity data from each well were normalized to the averaged fluorescence intensity of the first 6 time points of the experiment and the normalized fluorescence data for each replicate time point were averaged (n=6-12). The plots show normalized fluorescence intensity beginning at the moment of $Tl^+$ stimulus addition.
Figure 6A:
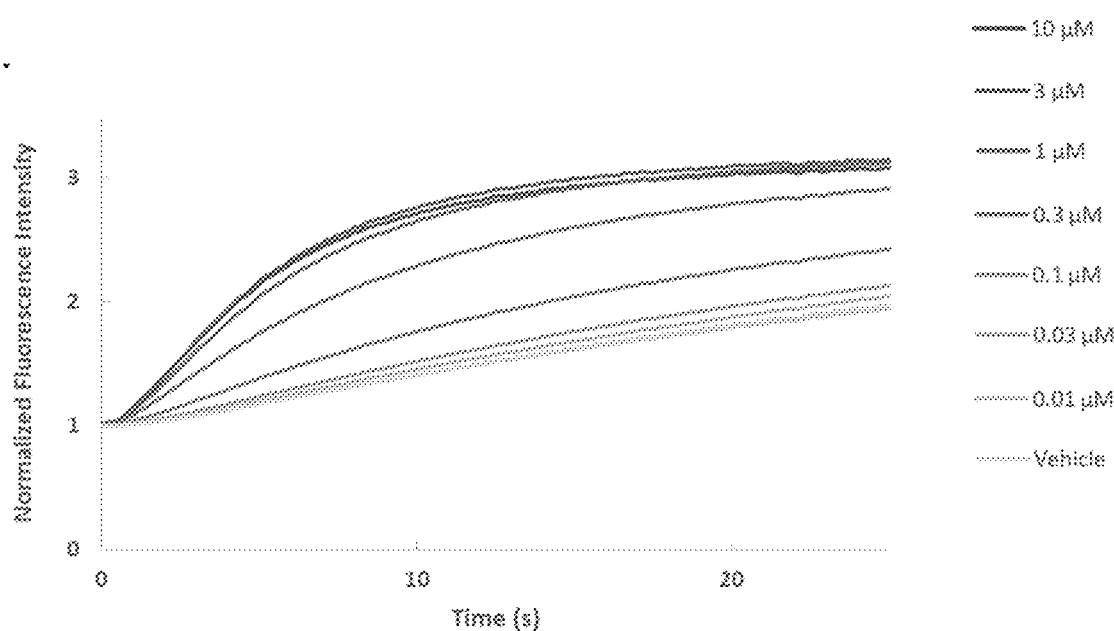
FIG. 6A and FIG. 6B show the comparison of data obtained during a $Tl^+$ flux assay to generate a ML297 concentration response curve using 8c as the indicator and 529/24 nm excitation and 565/24 nm emission filters (FIG. 6A) and 544/24 nm excitation and 593/40 nm emission filters (FIG. 6B). Fluorescence intensity data from each well were normalized to the averaged fluorescence intensity of the first 6 time points of the experiment and the normalized fluorescence data for each replicate time point were averaged (n=6-12). The plots show normalized fluorescence intensity after addition of $Tl^+$ stimulus.
Figure 6B:
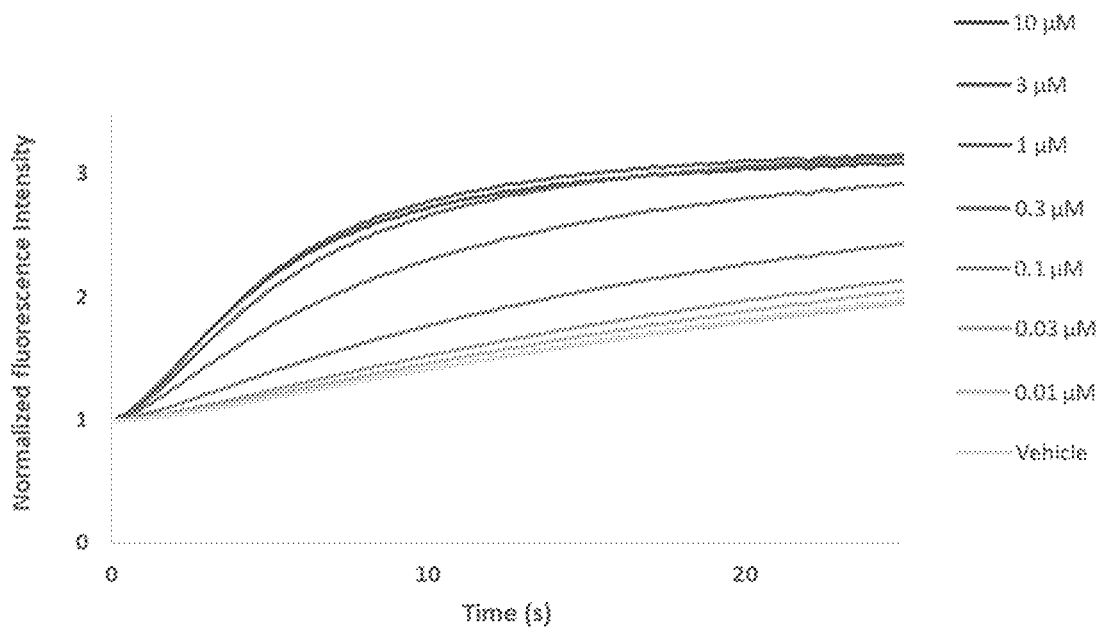

Using the same cell line and GIRK activator, 8c was also compared to the commercially available, red-shifted $Tl^+$ sensor FluxOR Red (Molecular Probes). Following the manufacturer's procedure, which requires supplementation of assay and stimulus buffers with a proprietary background suppressor, FluxOR Red exhibited a 5.37±0.001-fold increase in fluorescence at the highest concentration of ML297 compared to Thallos (4.30±0.008-fold increase) and 8c (3.09±0.004-fold increase). However, omission of the FluxOR Red background suppressor resulted in a significantly diminished increase in fluorescence of 1.17±0.007 at the highest ML297 concentration for FluxOR Red while Thallos and 8c only showed modest decreases in the absence of background suppressor (2.80±0.009 and 2.87±0.004-fold increases in fluorescence, respectively, FIG. 5). In addition, 8c exhibited a comparable dynamic range and $EC_{50}$ results using 544/24 nm excitation and 593/40 nm emission filters indicating 8c can also be used very effectively with longer wavelength, off-peak filters (FIGS. 6A-6B).

Strict adherence to the FluxOR Red protocol may not be compatible with or convenient for screening certain channels or transporters. For example, many buffers for $Tl^+$ flux assays, including those in most commercial kits, utilize gluconate as the primary anion due to the insolubility of $Tl^+$ in $Cl^-$ containing buffers. However, gluconate-based buffers may not be optimal for all targets and assay systems. In addition, the components of extracellular fluorescence masking dyes may affect the pharmacology of targets of interest. Tolerance of the $Tl^+$ sensing dye towards varied assay conditions would allow greater flexibility for screening. The performance of 8c, Thallos, and FluxOR Red were compared using a bicarbonate-based stimulus buffer with 500 μM of $Tl^+$ under two conditions. First, an automation compatible "no-wash" procedure was tested where the wash step after dye loading was omitted and all buffers were supplemented with 1 mM of Allura Red AC to suppress extracellular fluorescence. Under these conditions, 8c and Thallos exhibited 3.40±0.009 and 3.83±0.007-fold increases in fluorescence and ML297 $EC_{50}$s of 204±5.2 nM and 219±23 nM, respectively, were calculated. In contrast, FluxOR Red exhibited no change in fluorescence upon $Tl^+$ addition and the data could not be fit to a CRC. Second, using similar conditions omitting Allura Red AC while employing a wash step after dye loading produced comparable results (FIG. 5 and Table 3). These data demonstrate the utility of 8c in assays where extracellular fluorescence masking dyes are not compatible or where "no wash" procedures are desirable.

TABLE 3

$pEC_{50}$ and standard error of ML297 activation of GIRK1 and GIRK2 co-expressing HEK-293 cells determined from concentration response curves fit using data obtained under the corresponding conditions.

| Dye | FluxOR Red Kit Background Suppressor | | $HCO_3^-$ Stimulus Buffer 1 mM Allura Red AC | |
|---|---|---|---|---|
| | + | − | + | − |
| Thallos | 6.57 ± 0.04 | 6.65 ± 0.02 | 6.66 ± 0.01 | 6.61 ± 0.01 |
| FluxOR Red | 6.64 ± 0.01 | 6.41 ± 0.03 | ND | 7.02 ± 0.1 |
| 8c | 6.59 ± 0.01 | 6.61 ± 0.02 | 6.69 ± 0.01 | 6.59 ± 0.03 |
| 8c (544x/593m) | 6.63 ± 0.01 | 6.66 ± 0.04 | — | — |

In conclusion, dimethyl rhodol 8c has been identified from a series of rhodol-based $Tl^+$ sensors as a versatile reagent for $Tl^+$ flux assays. It localizes to the cytoplasm similarly to Thallos while exhibiting greater pH tolerance and excitation and emission spectra red-shifted ~30 nm. 8c exhibits an excellent dynamic range using both on-peak and longer off-peak filter sets and is compatible with a variety of assay conditions.

The foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

We claim:

1. A compound of the following formula,

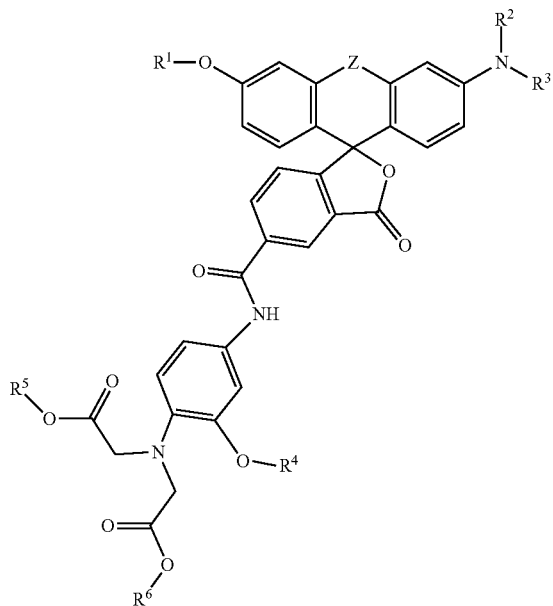

or a salt thereof,
wherein:

Z is O, CR$^x$R$^y$, SiR$^x$R$^y$, or SO$_2$;

R$^1$ is C$_{1-10}$alkyl-C(O)—;

—NR$^2$R$^3$ is —NHC(O)CH$_3$, —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, —NH-cyclohexyl, —NH—CH$_2$CH$_2$CH$_2$CH$_3$, —NH-phenyl, azetidin-1-yl, 3,3-difluoroazetidin-1-yl, pyrrolidin-1-yl, or piperidin-1-yl;

R$^4$ is C$_{1-10}$alkyl;

R$^5$ and R$^6$ are each independently C$_{1-6}$alkyl, —C$_{1-4}$-alkylene-O—R$^z$, —C$_{1-4}$-alkylene-O—C(O)—R$^z$, or —C$_{1-4}$-alkylene-O—C(O)—O—R$^z$;

R$^x$ and R$^y$ are each independently C$_{1-4}$alkylene; and

R$^z$, at each occurrence, is independently C$_{1-6}$alkyl, C$_{3-10}$cycloalkyl, C$_{6-20}$aryl, or a 4 to 8-membered heterocycle, wherein the C$_{3-10}$cycloalkyl, C$_{6-20}$aryl, and 4 to 8-membered heterocycle are optionally substituted with one or more substituents independently selected from the group consisting of halogen, C$_{1-4}$haloalkyl, —CN, C$_{1-4}$alkyl-O—, C$_{1-4}$alkyl-C(O)—NH—, and C$_{1-4}$alkyl-NH—C(O)—.

2. The compound of claim 1, or a salt thereof, wherein Z is O.

3. The compound of claim 1, or a salt thereof, wherein R$^1$ is C$_{1-4}$alkyl-C(O)—.

4. The compound of claim 1, or a salt thereof, wherein R$^4$ is C$_{1-4}$alkyl.

5. The compound of claim 1, or a salt thereof, wherein —NR$^2$R$^3$ is —N(CH$_3$)$_2$.

6. The compound of claim 1, or a salt thereof, wherein R$^5$ and R$^6$ are independently —C$_{1-4}$-alkylene-O—C(O)—R$^z$, and each R$^z$ is independently C$_{1-6}$alkyl.

7. The compound of claim 1, or a salt thereof, wherein each of R$^5$ and R$^6$ is —CH$_2$—O—C(O)—CH$_3$.

8. The compound of claim 1, having a structure of formula (I-a), or a salt thereof,

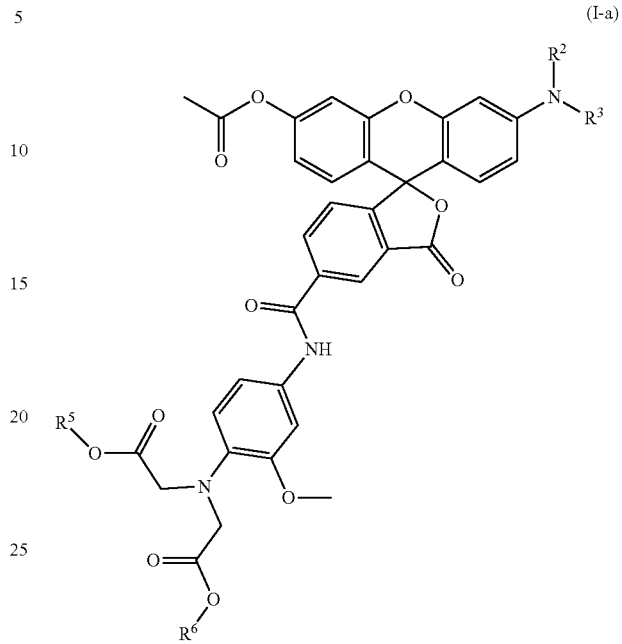

wherein —NR$^2$R$^3$, R$^5$, and R$^6$ are as defined in claim 1.

9. The compound of claim 1, selected from the group consisting of bis(acetoxymethyl) 2,2'-((4-(3'-acetamido-6'-acetoxy-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(dimethylamino)-3-oxo-3H-spiro[isobenzofuran-1,9'-xanthene]-5-carboxamido)-2-methoxyphenyl)azanediyl)diacetate;

bis(acetoxymethyl) 2,2'-((4-(3'-acetoxy-6'-(diethylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(dipropylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(dibutylamino)-3-oxo-3H-spiro[isobenzofuran-1,9'-xanthen]-5-ylcarboxamido)-2-methoxyphenyl)azanediyl)diacetate;

bis(acetoxymethyl) 2,2'((4-(3'-acetoxy-6'-(cyclohexylamino)-3-oxo-3H-spiro[isobenzofuran-1,9'-xanthen]-5-ylcarboxamido)-2-methoxyphenyl)azanediyl)diacetate;

bis(acetoxymethyl) 2,2'((4-(3'-acetoxy-6'-(butylamino)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-3-oxo-6'-(phenylamino)-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-6'-(azetidin-1-yl)-3-oxo-3H-spiro[isobenzofuran-1,9'-xanthen]-5-ylcarboxamido)-2-methoxyphenyl)azanediyl)diacetate;

bis(acetoxymethyl) 2,2'((4-(3'-acetoxy-6'-(3,3-difluoroazetidin-1-yl)-3-oxo-3H-spiro[isobenzofuran-1,9'-xanthen]-5-ylcarboxamido)-2-methoxyphenyl)azanediyl)diacetate;

bis(acetoxymethyl) 2,2'-((4-(3'-acetoxy-3-oxo-6'-(pyrrolidin-1-yl)-3H-spiro[isobenzofuran-1,9'-xanthen]-5-yl-carboxamido)-2-methoxyphenyl)azanediyl)diacetate; and bis(acetoxymethyl) 2,2'-((4-(3'-acetoxy-3-oxo-6'-(piperidin-1-yl)-3H-spiro[isobenzofuran-1,9'-xanthen]-5-yl-carboxamido)-2-methoxyphenyl)azanediyl)diacetate, or a salt thereof.

10. The compound of claim 9 that is bis(acetoxymethyl) 2,2'-((4-(3'-acetoxy-6'-(dimethylamino)-3-oxo-3H-spiro[isobenzofuran-1,9'-xanthene]-5-carboxamido)-2-methoxyphenyl)azanediyl)diacetate, or a salt thereof.

11. A method of preparing the compound of claim 1, or a salt thereof, the method comprising reacting a compound of the following formula

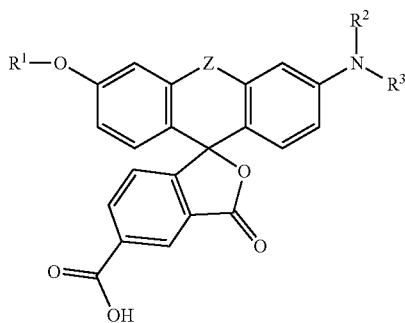

with a compound of the following formula

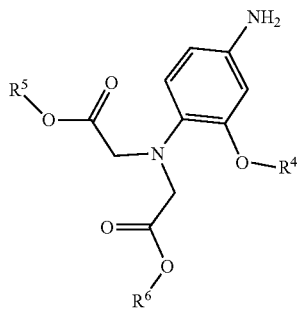

to provide the compound of claim 1, or salt thereof.

12. The method of claim 11, further comprising converting a compound of the following formula

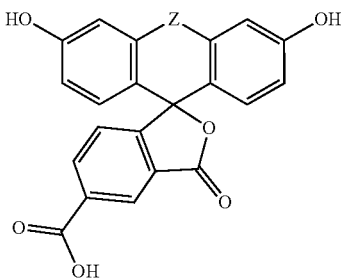

to the compound of formula

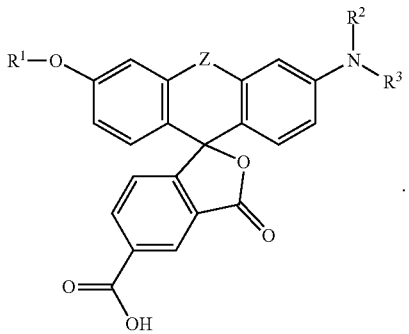

13. The method of claim 11, wherein Z is O.

14. A method of detecting flux of a metal ion into a cell, the method comprising
(a) contacting the cell with a compound of the following formula:

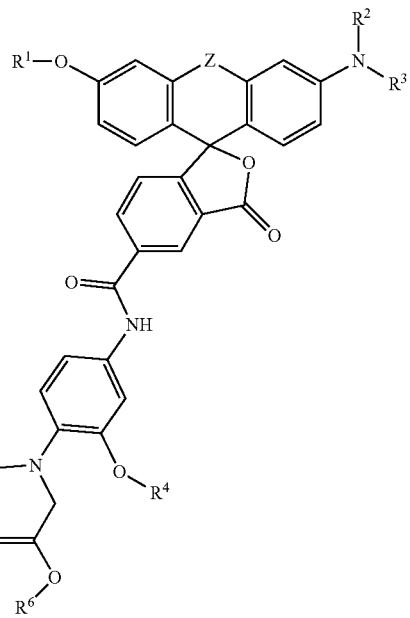

or a salt thereof,
wherein:
Z is O;
$R^1$ is $C_{1-10}$alkyl-C(O)—;
—$NR^2R^3$ is —$N(CH_3)_2$, —$N(CH_2CH_3)_2$, —$N(CH_2CH_2CH_3)_2$, —$N(CH_2CH_2CH_2CH_3)_2$, —NH-cyclohexyl, —NH—$CH_2CH_2CH_2CH_3$, azetidin-1-yl,3,3-difluoroazetidin-1-yl, pyrrolidin-1-yl, or piperidin-1-yl;
$R^4$ is $C_{1-10}$alkyl;
$R^5$ and $R^6$ are each independently $C_{1-6}$alkyl, —$C_{1-4}$-alkylene-O—$R^z$, —$C_{1-4}$-alkylene-O—C(O)—$R^z$, or —$C_{1-4}$-alkylene-O—C(O)—O—$R^z$; and
$R^z$, at each occurrence, is independently $C_{1-6}$alkyl, $C_{3-10}$cycloalkyl, $C_{6-20}$aryl, or a 4 to 8-membered heterocycle, wherein the $C_{3-10}$cycloalkyl, $C_{6-20}$aryl, and 4 to 8-membered heterocycle are optionally substituted with one or more substituents independently selected from the group consisting of halogen, $C_{1-4}$haloalkyl, —CN, $C_{1-4}$alkyl-O—, $C_{1-4}$alkyl-C(O)—NH—, and $C_{1-4}$alkyl-NH—C(O)—;
(b) subsequently contacting the cell with the metal ion; and
(c) subsequently measuring fluorescence produced by the cell.

15. The method of claim 14, wherein the metal ion is $Tl^+$.

16. The method of claim 14, wherein the cell comprises at least one ion channel.

17. The method of claim 16 wherein the at least one ion channel comprises a potassium channel.

18. The method of claim 14, further comprising measuring fluorescence produced by the cell after step (a) and before step (b).

* * * * *